(12) United States Patent
Rank et al.

(10) Patent No.: US 8,795,961 B2
(45) Date of Patent: Aug. 5, 2014

(54) PREPARATIONS, COMPOSITIONS, AND METHODS FOR NUCLEIC ACID SEQUENCING

(75) Inventors: David R. Rank, Pacific Grove, CA (US); Paul Peluso, San Carlos, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 434 days.

(21) Appl. No.: 12/553,478

(22) Filed: Sep. 3, 2009

(65) Prior Publication Data

US 2010/0081143 A1    Apr. 1, 2010

Related U.S. Application Data

(60) Provisional application No. 61/094,837, filed on Sep. 5, 2008.

(51) Int. Cl.
*C12Q 1/68* (2006.01)
*C12P 19/34* (2006.01)

(52) U.S. Cl.
USPC .......................................... 435/6.1; 435/91.1

(58) Field of Classification Search
None
See application file for complete search history.

(56) References Cited

U.S. PATENT DOCUMENTS

| | | | |
|---|---|---|---|
| 5,001,050 A | 3/1991 | Blanco et al. | |
| 5,198,543 A | 3/1993 | Blanco et al. | |
| 5,547,839 A | 8/1996 | Dower et al. | |
| 5,576,204 A | 11/1996 | Blanco et al. | |
| 5,648,245 A | 7/1997 | Fire et al. | |
| 5,674,716 A | 10/1997 | Tabor et al. | |
| 5,714,320 A | 2/1998 | Kool | |
| 5,723,584 A | 3/1998 | Schatz | |
| 5,874,239 A | 2/1999 | Schatz | |
| 5,932,433 A | 8/1999 | Schatz | |
| 6,210,891 B1 | 4/2001 | Nyren et al. | |
| 6,210,896 B1 | 4/2001 | Chan et al. | |
| 6,255,083 B1 | 7/2001 | Williams | |
| 6,258,568 B1 | 7/2001 | Nyren | |
| 6,261,808 B1 | 7/2001 | Auerbach | |
| 6,265,552 B1 | 7/2001 | Schatz | |
| 6,323,009 B1 | 11/2001 | Lasken et al. | |
| 6,787,308 B2 | 9/2004 | Balasubramanian et al. | |
| 6,833,246 B2 | 12/2004 | Balasubramanian et al. | |
| 6,917,726 B2 | 7/2005 | Levene et al. | |
| 7,056,661 B2 | 6/2006 | Korlach et al. | |
| 7,170,050 B2 | 1/2007 | Turner et al. | |
| 7,270,951 B1 | 9/2007 | Stemple et al. | |
| 7,361,466 B2* | 4/2008 | Korlach et al. | ............ 435/6.1 |
| 7,476,503 B2 | 1/2009 | Turner et al. | |
| 2001/0046681 A1 | 11/2001 | Senapathy | |
| 2003/0044781 A1 | 3/2003 | Korlach et al. | |
| 2003/0096253 A1 | 5/2003 | Nelson et al. | |
| 2003/0190647 A1 | 10/2003 | Odera | |
| 2003/0207267 A1 | 11/2003 | Lasken et al. | |
| 2003/0215862 A1 | 11/2003 | Parce et al. | |
| 2004/0038206 A1 | 2/2004 | Zhang et al. | |
| 2004/0048300 A1 | 3/2004 | Sood et al. | |
| 2004/0152119 A1 | 8/2004 | Sood et al. | |
| 2004/0175761 A1 | 9/2004 | Balasubramanian et al. | |
| 2004/0224319 A1 | 11/2004 | Sood et al. | |
| 2004/0259082 A1 | 12/2004 | Williams | |
| 2005/0260609 A1 | 11/2005 | Lapidus | |
| 2007/0099212 A1 | 5/2007 | Harris | |
| 2009/0024331 A1 | 1/2009 | Tomaney et al. | |

FOREIGN PATENT DOCUMENTS

| | | |
|---|---|---|
| WO | 91/06678 A1 | 5/1991 |
| WO | 96/27025 A1 | 9/1996 |
| WO | 99/05315 A2 | 2/1999 |
| WO | 2004/070005 A2 | 8/2004 |

OTHER PUBLICATIONS

Raja et al. DNA sequencing using differential extension with nucleotide subsets (DENS). Nucleic Acids Res. (1997) vol. 25, No. 4, pp. 800-805.*
Blanco, et al, (1985) Replication of phage Φ29 DNA with purified terminal protein and DNA polymerase: Synthesis of full-length Φ29 DNA Proc. Natl. Acad. Sci. USA 82:6404-6408.
Carusi, E.A. (1977) Virology 76:380-394.
Dean FB, et al. Rapid amplification of plasmid and phage DNA using Phi 29 DNA polymerase and multiply-primed rolling circle amplification. Genome Res Jun. 2001; 11(6) 1095-9.
Eid et al.; Science 323:133-138 (Jan. 2, 2009).
Harding, et al. (1980) Virology 104:323-338.
Inciarte, et al. (1980) J. Virol. 34:187-199.
Levene et al., Science 299 (5607):682-686 (2003).
John R. Nelson, et al., "TempliPhi, Φ29 DNA Polymerase Based Rolling Circle Amplification of Templates for DNA Sequencing," BioTechniques 32:S44-S47 (Jun. 2002).
Peñalva, et al. (1982) Initiation of phage Φ29 DNA replication in vitro: Formation of a covalent complex between the terminal protein, p3, and 5'-dAMP. Proc. Natl. Acad. Sci. USA 79:5522-5526.
Michael J. Reagin, et al., "TempliPhi: A Sequencing Template Preparation Procedure That Eliminates Overnight Cultures and DNA Purification." J Biomol Tech. Jun. 2003; 14(2): 143-148.
Rekosh, et al. (1977) Cell 11:283-295.
International Search Report and Written Opinion dated May 11, 2010 for related case PCT/US2009/005013.
International Preliminary Report on Patentability dated Mar. 17, 2011 for related case PCT/US2009/005013.

* cited by examiner

*Primary Examiner* — Kenneth R. Horlick
*Assistant Examiner* — David Thomas
(74) *Attorney, Agent, or Firm* — Deana A. Arnold

(57) ABSTRACT

Preparations, compositions and methods of sequencing nucleic acids are provided. The preparations, methods and compositions employ multiple priming sites on a target nucleic acid and typically utilize single molecule sequencing processes to identify sequence portions of the target which are then assembled to obtain the sequence of the target.

28 Claims, 8 Drawing Sheets

PREPARATIONS, COMPOSITIONS, AND METHODS FOR NUCLEIC ACID SEQUENCING

CROSS-REFERENCE TO RELATED APPLICATIONS

This application claims the benefit of U.S. Provisional Application No. 61/094,837, filed Sep. 5, 2008, the disclosure of which is incorporated herein by reference in its entirety for all purposes.

STATEMENT REGARDING FEDERALLY SPONSORED RESEARCH

The U.S. government has a paid-up license in this invention and the right in limited circumstances to require the patent owner to license others on reasonable terms as provided for by the terms of Grant No. 1 R01 HG003710-01 awarded by the National Human Genome Research Institute (NHGRI) of the National Institutes of Health (NIH).

BACKGROUND OF THE INVENTION

The ability to understand the genetic code that serves as the blueprint for the framework of all life has yielded countless advances in countless areas. From the ability to diagnose disease to the ability to identify evolutionary connections and/or diversity, to the ability to manipulate the genetic framework in the development of new materials and compositions, this understanding has opened doors to innumerable advances that have benefited and will continue to benefit the human race.

Integral to these advances have been the advances in technology directed to the reading and/or characterization of the genetic code. For example, development of nucleic acid sequencing technologies has allowed for the base-by-base identification of the nucleic acid sequences that make up the genetic code, allowing the large-scale sequencing of the human genome. The sequence information generated is useful in studying fundamental biological processes, developing diagnostics and theranostics, and performing forensic research. Other advances include rapid array-based technologies that allow reasonably facile identification of genetic patterns from patients or other biological samples.

With each technological advance, there exist opportunities to further improve the state of the art through advances in related or ancillary technologies associated with those advanced areas. For example, advances in fluorescent dye chemistries have fueled many advances in genetic technologies by permitting simple optical analyses of biological reactions and their products. Likewise, development of microfluidic technologies have provided for advances in fluid and reagent handling to yield a reproducibility that had not been previously achievable through more conventional means.

The present invention is directed to improved preparations, processes, systems, and compositions used in genetic analysis that can yield enhanced accuracy and ease of use in such analyses.

BRIEF SUMMARY OF THE INVENTION

The present invention provides preparations, compositions and methods for use in nucleic acid analyses, and particularly in determining the sequence of nucleotides in target nucleic acids. The present invention generally comprises multiply priming target nucleic acids and/or fragments derived from those target nucleic acids using randomly generated and/or predefined/pre-identified primers. The methods, preparations, and compositions of the invention provide facile sample preparation processes for a variety of analytical applications, and particularly in sequence-by-incorporation processes.

In certain aspects, the invention provides methods of sequencing nucleic acids. In certain embodiments, sequencing methods of the invention comprise providing a sample that includes target nucleic acids, adding a set of primers having different nucleotide compositions from one another, and contacting the target nucleic acids with the primers under hybridization conditions to generate target-primer complexes. In certain preferred embodiments, some or all of the target-primer complexes comprise multiple primers. Template-directed synthesis is initiated from only one primer hybridized to each target-primer complex to generate a single nascent nucleic acid strand complementary to each molecule of target nucleic acid. The template-directed synthesis reaction is monitored and incorporation of nucleotides into the nascent nucleic acid strands is detected and the nucleotide sequences of the nascent nucleic acid strands is identified. The nucleotide sequences of the nascent nucleic acid strands is used to determine the nucleotide sequences of the target nucleic acids, e.g., by complementarity.

In certain preferred embodiments, template-directed synthesis for each target nucleic acid is carried out at a separate reaction site from the template-directed synthesis for each other target nucleic acid. For example, each target-primer complex can be confined to a separate reaction site on a substrate comprising a plurality of reaction sites, e.g., by direct or indirect immobilization of target nucleic acids, primers, and/or enzymes. In preferred embodiments, each reaction site on a substrate is positioned such that a signal emitted from any one reaction site is optically resolvable from any other signal emitted from any other of the reaction sites on the substrate. For example, a fluorescence emission detected during a template-directed synthesis reaction confined to a single reaction site is optically resolvable from any other fluorescence emission from any other reaction site, thereby allowing a series of fluorescence emissions from a single reaction site to be detected and unambiguously assigned to the single reaction site. In some embodiments, the substrate includes optical confinements, each of which provides a single reaction site. Signals detected from single target-primer complexes are indicative of the identity of a nucleotide incorporated during the template-directed synthesis. As such, a sequence of signals from a single target-primer complex is indicative of a sequence of nucleotides incorporated into the nascent strand, and is therefore also indicative (by complementarity) of the sequence of the target nucleic acid serving as the template in the synthesis reaction.

In some aspects, template-directed synthesis reactions can include buffer exchange steps between nucleotide incorporation event (e.g., flush-and-scan methods), or may be carried out with no intervening buffer exchange steps to detect nucleotide incorporation events in a processive polymerization reaction in real time. Enzymes catalyzing such reactions are typically polymerases, and include DNA polymerases, RNA polymerases, and reverse transcriptases. In certain embodiments, the enzymes are highly processive, thermostable, and/ or capable of strand displacement. Nucleic acids for use in the methods described herein (e.g., primers and/or target nucleic acids) may or may not be amplified, cloned, fragmented, or otherwise modified. Sets of primers may be randomly generated, e.g., in applications in which the sequence of the target nucleic acid is not known prior to the template-directed synthesis reaction. Alternatively, sets of primers may be specifically designed to anneal to one or more selected portions of one or more target nucleic acids, e.g., in applications in which some or all of the sequence of the target nucleic acid was previously determined.

In further aspects, the invention provides methods for generating a set of overlapping sequence reads for a target nucleic acid. In certain embodiments, such methods include annealing a plurality of different primers to anneal to multiple nucleic acid templates derived from target nucleic acids (e.g., by amplification or fragmentation of the target nucleic acid), and subjecting the templates to template-directed sequencing reactions in which only a single of potentially multiple primers bound to a given template is extended by a polymerase. Limitation of primer extension to only one primer on a given template can be accomplished in various ways, e.g., by limiting the number of polymerases that have access to the template complex. In certain preferred embodiments, polymerases are immobilized at optically resolvable reaction sites and exposed to a reaction mixture containing nucleic acid templates, and therefore a single template is bound by a single polymerase and primer extension takes place from a single primer. Incorporation of nucleotides into a nascent strand complementary to the template is monitored by detecting signals emitted from the polymerase complex, and the signals are subjected to statistical analysis to identify a sequence of nucleotides incorporated into each of the growing nascent strands. Nucleotide sequences complementary to the sequences of nucleotides incorporated into the nascent strands, each of which was generated on a different one of the plurality of nucleic acid templates, are used to generate a set of overlapping sequence reads for the target nucleic acid. In certain embodiments, a set of sequence reads is subjected to statistical analysis, thereby determining a consensus nucleotide sequence of the target nucleic acid.

In certain aspects, methods of generating sequence information for a target nucleic acid are provided. Such methods typically involve providing a plurality of nucleic acid templates that correspond to the target nucleic acid, multiple primers that anneal to the templates, and annealing the multiple primers to multiple locations within the templates. Each of the primer-bound templates is contacted with a single polymerase that binds at a single primer annealed to the template, and a sequence-by-synthesis reaction is performed to determine the nucleotide sequence of the templates, e.g., by complementarily to the sequence of nucleotides incorporated into the nascent strand. An overall nucleotide sequence of the target nucleic acid can then be assembled from the nucleotide sequences of the templates.

In certain embodiments the nucleic acid templates corresponding to the target nucleic acid include multiple overlapping fragments with nucleotide sequences identical to portions of the target nucleic acid. In some embodiments, the nucleic acid templates are circular nucleic acid templates that are repeatedly processed in the sequence-by-synthesis reactions to generate multiple copies of the nucleotide sequences of the nucleic acid templates, e.g., when a polymerase catalyzing the reaction is capable of strand displacement. In some embodiments, the nucleic acid templates are linear nucleic acids and the annealing and sequencing steps are performed multiple times to generate multiple nucleotide sequence reads from each of the nucleic acid templates downstream of multiple single primers annealed to the nucleic acid templates. In certain preferred embodiments, multiple sequence-by-synthesis reactions are performed simultaneously in an array of reaction sites (e.g., an array of optical confinements), each of which contains a single one of the templates.

The invention further provides compositions for sequencing target nucleic acids. In preferred embodiments, the compositions include a set of nucleic acid templates derived from the target nucleic acid (e.g., by fragmentation, amplification, purification of cloned target nucleic acid, etc.), a set of random primers annealed to the templates, and polymerase enzymes individually immobilized at optically resolvable reaction sites on a substrate, each of which is bound to one of the nucleic acid templates at one of the random primers annealed thereto. Such compositions also include a set of different types of differentially labeled nucleotides, each of which carries a label that emits a signal that is specific to its type that is detectable at the optically resolvable reaction sites.

DETAILED DESCRIPTION OF THE INVENTION

I. General

Figure 1:
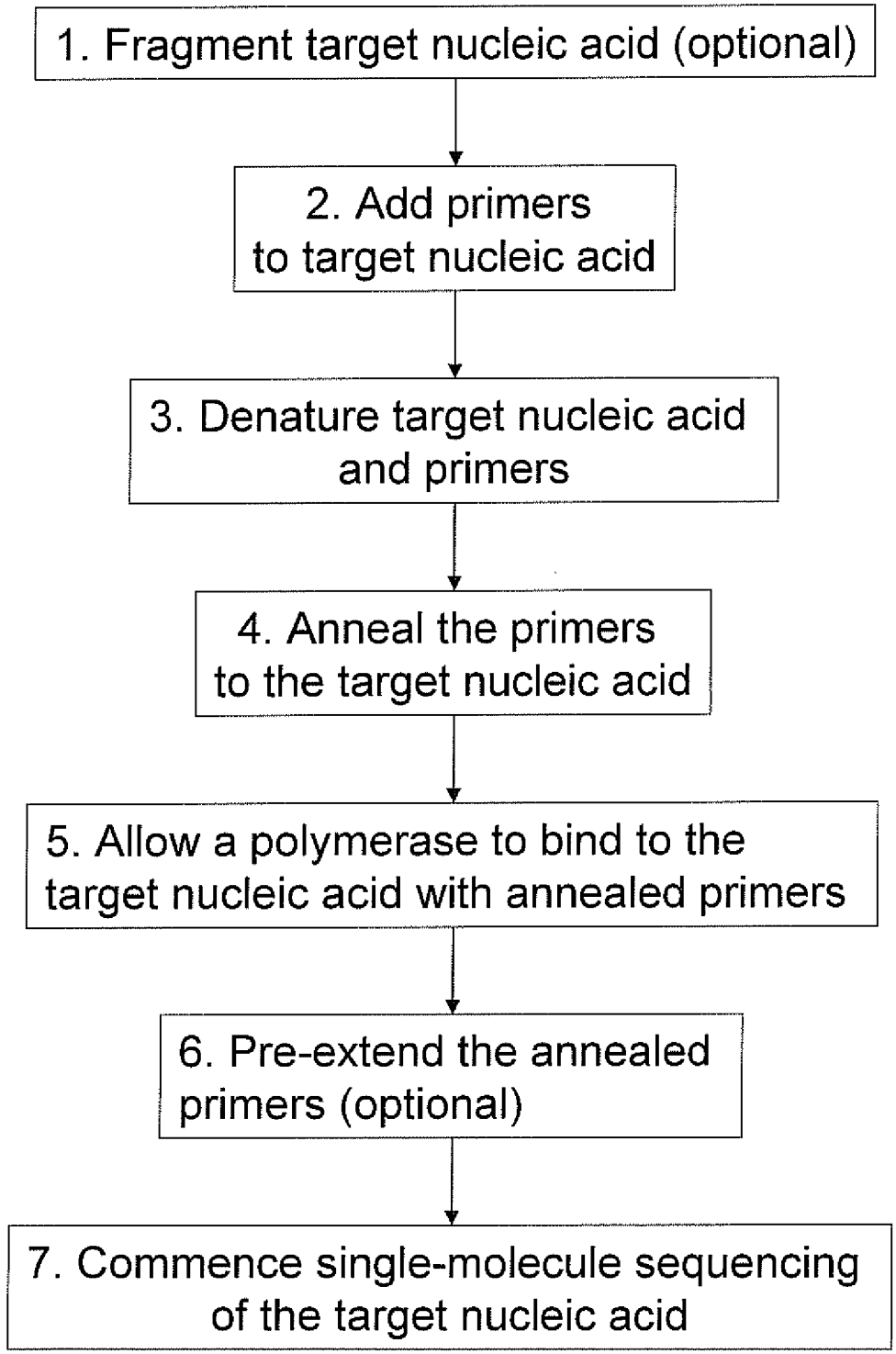
FIG. 1 schematically illustrates the process flow for one aspect of the invention.

The present invention is generally directed to improved preparations, methods, systems, and compositions for carrying out nucleic acid sequence analysis, and particularly sequence analysis that employs template-dependent synthesis in identifying the nucleotide sequence of target or template nucleic acids. Nucleic acid sequence analysis that employs template-dependent synthesis identifies individual bases, or groups of bases, as they are added during a template-mediated synthesis reaction (e.g., a primer extension reaction), where the reaction is monitored to identify each base added to a nascent nucleic acid molecule that is complementary to the target nucleic acid template. In doing so, the sequence of the template nucleic acid is also determined by complementarity to the nascent strand being synthesized. Other such processes include ligation-driven processes, where oligo- or polynucleotides are complexed with an underlying template nucleic acid, in order to identify the sequence of nucleotides in that nucleic acid. Typically, such processes are enzymatically mediated using nucleic acid polymerases, such as DNA polymerases, RNA polymerases, reverse transcriptases, and the like, or other enzymes such as in the case of ligation-driven processes, e.g., ligases.

Sequence analysis using template-dependent synthesis can include a number of different processes. For example, one of the earliest methods for DNA sequencing was the four-color chain-termination Sanger sequencing methodology in which a population of template molecules is used to create a population of complementary fragments. Primer extension is carried out in the presence of the four naturally occurring nucleotides, and with a sub-population of dye-labeled terminator nucleotides, e.g., dideoxyribonucleotides, where each type of terminator (ddATP, ddGTP, ddTTP, ddCTP) includes a different detectable label. As a result, a nested set of fragments is created where the fragments terminate at each nucleotide in the template beyond the primer, and are labeled in a manner that permits identification of the terminating nucleotide. The nested fragment population is then subjected to size-based separation, e.g., using capillary electrophoresis, and the labels associated with each different sized fragment is identified to identify the terminating nucleotide. As a result, the sequence of labels moving past a detector in the separation system provides a direct readout of the sequence information of the synthesized fragments, and by complementarity, the underlying template (See, e.g., U.S. Pat. No. 5,171,534, incorporated herein by reference in its entirety for all purposes).

Other examples of template-dependent sequencing methods include sequence-by-synthesis processes, where individual nucleotides are identified iteratively, as they are added to the growing primer extension product. These processes generally fall into two categories. In a first category, a nucleic acid synthesis complex is contacted with one or more nucleotides under conditions that permit the addition of a single base, and little or no extension beyond that base. The reaction is then interrogated or observed to determine whether a base was incorporated, and provide the identity of that base. The second category generally provides for the real-time observation of the addition of nucleotides to the growing nascent strand in an uninterrupted reaction process, e.g., without wash steps.

One example of the first category of processes is pyrosequencing, which is a sequence-by-synthesis process that identifies the incorporation of a nucleotide by assaying the resulting synthesis mixture for the presence of by-products of the sequencing reaction, namely pyrophosphate. In particular, a primer, polymerase template complex is contacted with a single type of nucleotide. If that nucleotide is incorporated, the polymerization reaction cleaves the nucleoside triphosphate between the $\alpha$ and $\beta$ phosphates of the triphosphate chain, releasing pyrophosphate. The presence of released pyrophosphate is then identified using a chemiluminescent enzyme reporter system that converts the pyrophosphate, with AMP, into ATP, then measures ATP using a luciferase enzyme to produce measurable light signals. Where light is detected, the base is incorporated, where no light is detected, the base is not incorporated. Following appropriate washing steps, the various bases are cyclically contacted with the complex to sequentially identify subsequent bases in the template nucleic acid. See, e.g., U.S. Pat. No. 6,210,891, incorporated herein by reference in its entirety for all purposes).

In certain other related processes, the primer-template-polymerase complex is immobilized upon a substrate and the complex is contacted with labeled nucleotides. In alternate configurations, the nucleotides are provided with and without removable terminator groups, and upon incorporation, the label is coupled with the complex and is thus detectable. In the case of terminator-bearing nucleotides, all four different nucleotides, bearing individually identifiable labels, are contacted with the complex. Incorporation of the labeled nucleotide arrests extension, by virtue of the presence of the terminator, and adds the label to the complex. The label and terminator are then removed from the incorporated nucleotide, and following appropriate washing steps, the process is repeated. In the case of non-terminated nucleotides, a single type of labeled nucleotide is added to the complex to determine whether it will be incorporated, as with pyrosequencing. Following removal of the label group on the nucleotide and appropriate washing steps, the various different nucleotides are cycled through the reaction mixture in the same process. See, e.g., U.S. Pat. No. 6,833,246, incorporated herein by reference in its entirety for all purposes). These template-directed sequencing methods that comprise one-at-a-time nucleotide incorporations, e.g., separated by buffer exchange or wash steps, are sometimes referred to as "flush-and-scan" methods, and are typically considered to be non-processive sequence-by-synthesis technologies.

As noted above, in the second category of sequence-by-synthesis processes, the incorporation of differently labeled nucleotides is observed in real time as template-dependent synthesis is carried out in a processive manner. In particular, an individual immobilized polymerase-template-primer complex is observed as fluorescently labeled nucleotides are incorporated, permitting real time identification of each added base as it is added. In this process, label groups are attached to a portion of the nucleotide that is cleaved during incorporation. For example, by attaching the label group to a portion of the phosphate chain removed during incorporation, i.e., a $\beta$, $\gamma$, or other terminal phosphate group on a nucleoside polyphosphate, the label is not incorporated into the nascent strand, and instead, natural DNA is produced. In preferred aspects, observation of individual molecules typically involves the optical confinement of the complex within a very small illumination volume. By optically confining the complex, one creates a monitored region in which randomly diffusing nucleotides are present for a very short period of time, while incorporated nucleotides are retained within the observation volume for longer as they are being incorporated. This strategy results in a characteristic signal associated with the incorporation event, which is also characterized by a signal profile that is specific for the base being added. In related aspects, interacting label components, such as fluorescent resonant energy transfer (FRET) dye pairs, are provided upon the polymerase or other portion of the complex and the incorporating nucleotide, such that the incorporation event puts the labeling components in interactive proximity, and a characteristic signal results that is, again, also specific for the base being incorporated (See, e.g., U.S. Pat. Nos. 7,056,661, 6,917,726, 7,033,764, 7,052,847, 7,056,676, 7,170,050, 7,361,466, 7,416,844 and Published U.S. Patent Application Nos. 2007-0134128 and 2009-0024331, the full disclosures of which are hereby incorporated herein by reference in their entirety for all purposes).

II. Sequencing Library Generation by Multiple Priming

The present invention provides novel preparations, compositions, methods, and systems for carrying out template-directed sequencing processes. While these compositions and methods have utility across all of the various template-directed processes described herein, far ease of discussion, they are being primarily discussed in terms of preferred single-molecule, real-time sequencing processes, in which they provide myriad benefits. In particular, the present invention is generally directed to the preparation of multiply-primed target nucleic acids and the use of such compositions to improve the efficiency of sequencing of the target nucleic acids. For example, in various aspects, the methods described are rapid and efficient, taking only minutes and using small amounts of target nucleic acid; they do not require amplification or cloning of the target nucleic acid; in some aspects, they do not require prior knowledge of the sequence of the target nucleic acid; and they require only minimal sample handling. This is in stark contrast to current sample preparation procedures for other sequencing processes, which require up to several days and/or amplification prior to sequencing.

The present invention is particularly suitable for technologies that provide single molecule resolution (e.g., single molecular complex resolution), such as sequencing technologies that monitor synthesis of a single nascent nucleic acid to generate a nucleotide sequence "read" that can be used, by complementarity, to deduce the nucleotide sequence of the template strand upon which the nascent strand was constructed. As used herein, a "template" or "nucleic acid template" generally refers to a substrate in a sequencing reaction whose nucleotide sequence directs synthesis of a complementary strand. For example, a polymerase enzyme incorporates nucleotides into a nascent strand that is complementary to a nucleic acid template to which it is bound. The term "target nucleic acid" generally refers to a nucleic acid of interest, and in particular one for which a nucleotide sequence is desired. In certain embodiments, a target nucleic acid can be used as a template nucleic acid, e.g., after isolation from a cell lysate or other sample source, and so these terms are sometimes used interchangeably. Alternatively or in addition, a target nucleic acid can be used to derive template nucleic acids, e.g., by fragmentation, amplification, replication in a cell culture, and the like. For example, the whole genomic DNA sequence of an organism may be considered to be a "target nucleic acid," while fragments of whole genomic DNA isolated from the organism may be referred to as nucleic acid templates, e.g., if the fragments are to be subjected to template-dependent polymerization. As such, a population of template nucleic acids corresponding to a target nucleic acid may comprise one or more copies of the entire target nucleic acid, or one or more portions thereof, or fragments or derivatives thereof, preferably in a form suitable for a template-directed sequencing technology.

In at least one aspect, target nucleic acid preparations of the invention can be annealed to multiple primers, which serve as initiation sites for synthesis of a complement to the strand on which the primer contacted by a polymerase is annealed. Such primers may be random or designed primers, and may be essentially any type of nucleic acid amendable to the methods presented herein. For example, a primer may comprise DNA, RNA, cDNA, peptide nucleic acid (PNA), amplified and/or fragmented nucleic acid, or derivatives thereof (e.g., chemically modified, labeled, recoded, bound to one or more proteins, or otherwise altered). For example, the primer may be bound to a protein involved in initiation of replication. The primer may be single- or double-stranded, and/or double-stranded with single-stranded regions (e.g., stem- and loop-structures). Further, the target nucleic acid preparations comprising multiple primers bound thereto can be subjected to subsequent purification steps, e.g., to remove unbound primers or small target fragments, prior to initiation of primer extension. Such size-selective purifications, including but not limited to various size-exclusion spin columns, chromatography, and gel-based techniques, are well known to those of ordinary skill in the art (see, e.g., Maniatis, et al., Molecular Cloning: A Laboratory Manual, Cold Spring Harbor, N.Y., pp. 280-281 (1982)), and are commercially available, e.g., from Clontech (Mountain View, Calif.) and GE Healthcare (Sunnyvale, Calif.).

Sets of primers for use as initiation sites may be chosen or designed in various ways, depending on the experimental objectives of the practitioner, e.g., which portions of a template (or template population) are to be targeted for complementary strand synthesis. For example, a first portion of a nucleic acid sample may be fragmented and used to prime a second "template" portion of the same nucleic acid sample where it is desired to prime across all nucleic acids in the sample. Alternatively, a portion of the nucleic acid sample can be selectively amplified to create amplified products of selected regions of the nucleic acids therein; such amplification products (or fragments thereof) used for priming the template population. For example, select portions of a template can be targeted by generating primers that hybridize only to certain regions of interest in the template, e.g., repetitive, intronic and/or exonic regions of a genomic nucleic acid sample, and may be designed to anneal to the sense strand, antisense strand, or both strands of the genomic nucleic acid sample. The ratio of primers relative to template nucleic acids can be adjusted to promote a preferred density of primers bound to the template. In certain embodiments, a set of primers is generated by fragmentation, e.g., of genomic DNA, a DNA library, or a mixture of nucleic acids from one or more sources. For example, genomic DNA from a first human population may be fragmented and used to prime genomic DNA from a second human population. Alternatively, genomic DNA from a human population may be fragmented and used to prime genomic DNA from a non-human population, or vice versa. A population of primers may also be generated by synthesizing multiple primers separately, and then creating preferred combinations of selected primers for specific experimental objectives. One of ordinary skill in the art will readily understand that a primer set may be designed is various ways and that the methods described herein should not be limited to any one method of primer design.

In certain aspects, one benefit of using random primers is that the sequence of the target nucleic acid need not be known. The length of the random primers used in the instant methods is typically six to nine bases, but may be adjusted by the skilled practitioner depending, e.g., on the target nucleic acid to which they must anneal. In certain preferred embodiments, nonomers (9-mers) have been shown to perform well as random primers. In other embodiments, the primers may be longer, e.g., between about 10 and 100 bases, 20 and 80 bases, 30 and 60 bases, or about 40-50 bases in length. In preferred embodiments, the size of the primers is small enough to favor annealing to the target nucleic acid over annealing to one another. In certain embodiments in which large nucleic acids are fragmented to produce primers, the primers will be a size characteristic of the fragmentation method used, for example, digestion with one or more nucleases (e.g., endonuclease(s), exonuclease(s), etc.), nebulizer, sonicator, and the like. The conditions under which fragmentation occurs can be modified to promote production of a desired size range of fragments, e.g., by changing reaction temperature, salt concentration, ion concentration by methods known in the art. In such embodiments, a particular range of fragments may be further isolated by methods well known in the art, e.g., gel purification, fractionation, etc. In some embodiments, the "randomness" of the primers may be altered, e.g., by changing the base composition, such as increasing the G-C content. In certain specific embodiments, the primers may be chemically modified. For example, they may contain one or more thiophosphate moieties at the 3' terminus to block the exonuclease activity of a polymerase, and/or they may have a photocaged 3' terminus to allow photo-initiation of the sequencing reaction. Although single-stranded primers are typically used, double-stranded or partially double-stranded primers may also be used, as noted above.

In some embodiments, the primers are synthesized by the practitioner of the methods presented herein using methods well known to those of skill in the art, e.g. using a DNA synthesizer such as those from Applied Biosystems (Foster City, Calif.). In other embodiments, the randomly synthesized primers are purchased from a third-party vendor, e.g., from New England Biolabs (Ipswich, Mass.) or Gene Link (Hawthorne, N.Y.).

As noted previously, in some cases, e.g., in re-sequencing applications and the like, the primers may be designed to provide optimal positioning over the target to be sequenced. In particular, based upon the expected sequence of the target, primers may be provided that prime the target nucleic acid in desired locations, e.g., at regularly spaced intervals, within or proximal to particular sequence motifs, and the like. For example, in some cases, primers may be designed to fall within or immediately adjacent to known repetitive regions within a target nucleic acid, e.g., a genome, in order to provide sequence readouts in the repeat regions to aid in assembly of the sequence data. Similarly, primers may be designed to target exonic regions, intronic regions, repetitive regions, or other regions of interest in a target nucleic acid on the sense, antisense, or both strands of the target nucleic acid. Alternatively, primers may be targeted to multiple regions of interest to facilitate characterization and/or identification of particular genetic sequences, e.g., in diagnostic applications, or to target specific genomic regions, e.g., specific types of chromosomes or regions within whole chromosomes, e.g., telomeres, centromeres, sex chromosomes, etc.

Figure 2:
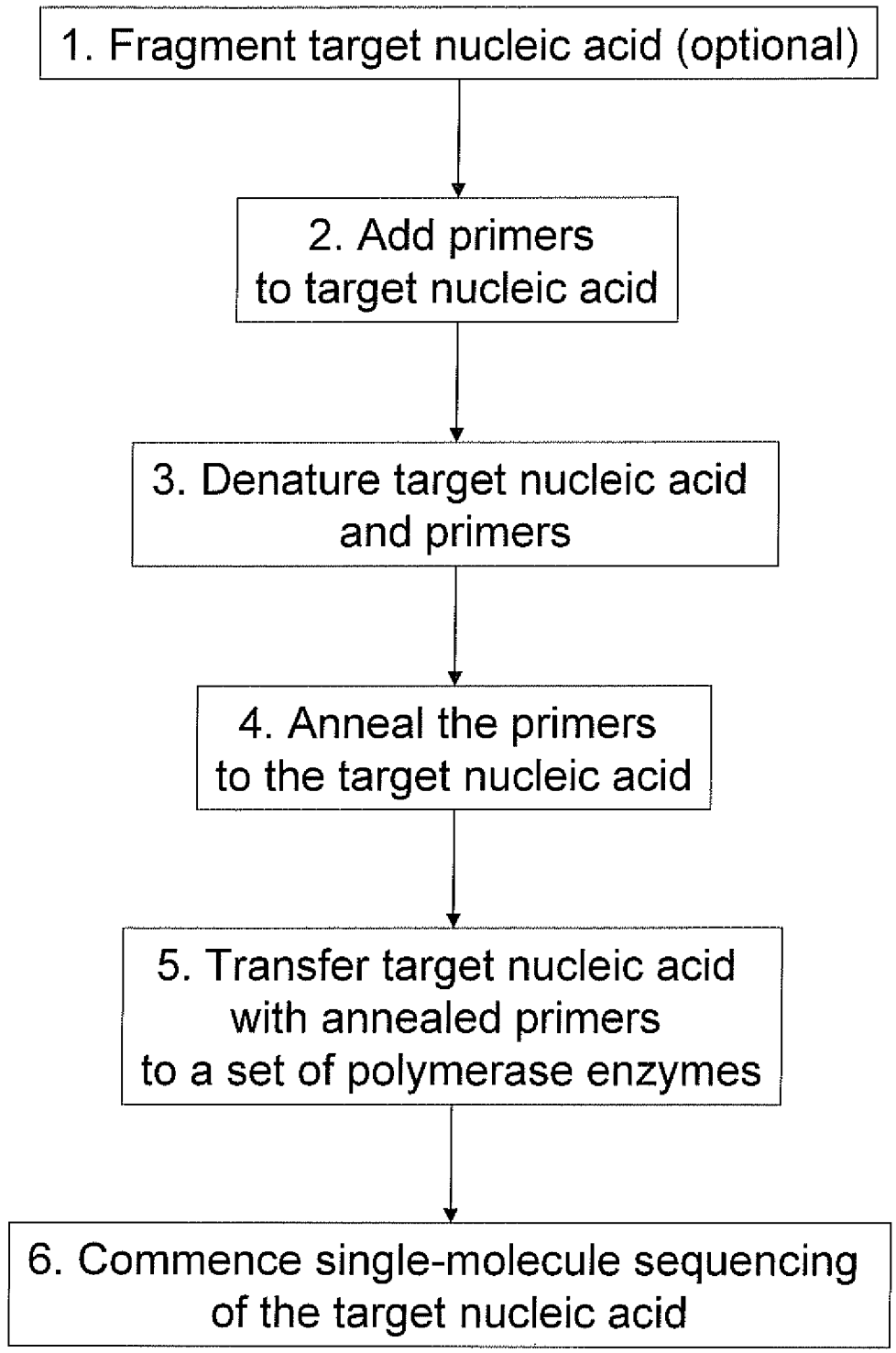
FIG. 2 schematically illustrates a process flow for an alternate process in accordance with the invention.

In alternative embodiments of the invention, the underlying target nucleic acid and/or its fragments are used in place of exogenously introduced primers, e.g., the target is self-priming. In particular, in at least one aspect, a double-stranded target nucleic acid may be nicked in a plurality of locations, where each nick site provides a priming location for a strand-displacing polymerase. Alternatively, by employing a slow-cool process during an annealing step, e.g., as shown in FIGS. 1 and 2, one may increase the likelihood of intra-fragment hybridization. Because the probability of a perfect match of a single-stranded fragment and its complement is extremely low, it will result in fragments that are partially double-stranded. These partially double-stranded fragments then provide suitable priming sites for the polymerase. A variety of additional embodiments are readily practiced in accordance with the scope of the invention.

In another aspect, the target nucleic acids used in the methods herein may be essentially any type of nucleic acid amendable to the methods presented herein. For example, a target nucleic acid may be DNA (e.g., genomic DNA, mtDNA, etc.), RNA (e.g., mRNA, siRNA, etc.), cDNA, peptide nucleic acid (PNA), amplified nucleic acid (e.g., via PCR, LCR, or whole genome amplification (WGA)), nucleic acid subjected to fragmentation and/or ligation modifications, whole genomic DNA or RNA, or derivatives thereof (e.g., chemically modified, labeled, recoded, protein-bound or otherwise altered). For example, a target nucleic acid may be bound to a protein involved in initiation of replication, e.g., Φ29 terminal protein p3 or adenovirus terminal protein, which are described in the art, e.g., in Blanco, et al. (1985) Proc. Natl. Acad. Sci. USA 82:6404-8; Peñalva, et al. (1982) Proc. Natl. Acad. Sci. USA 79:5522-6; Inciarte, et al. (1980) J. Virol. 34:187-199; Harding, et al. (1980) Virology 104:323-338; Rekosh, et al. (1977) Cell 11:283-295; and Carusi, E. A. (1977) Virology 76:390-4, the disclosures of which are incorporated herein by reference in their entireties for all purposes. The target nucleic acid may be linear, circular (including templates for circular redundant sequencing (CRS)), single- or double-stranded, and/or double-stranded with single-stranded regions (e.g., stem- and loop-structures). For example, certain preferred template structures are provided in U.S. Ser. No. 12/413,258, filed Mar. 27, 2009. The target nucleic acid may be purified or isolated from an environmental sample (e.g., ocean water, ice core, soil sample, etc.), a cultured sample (e.g., a primary cell culture or cell line), samples infected with a pathogen (e.g., a virus or bacterium), a tissue or biopsy sample, a forensic sample, a blood sample, or another sample from an organism, e.g., animal, plant, bacteria, fungus, virus, etc. Such samples may contain a variety of other components, such as proteins, lipids, and non-target nucleic acids. In certain embodiments, the target nucleic acid is a complete genomic sample from an organism. In other embodiments, the target nucleic acid is total RNA extracted from a biological sample or a cDNA library. As noted above, a target nucleic acid may be used directly in a template-directed sequencing reaction, or may be use to derive a population of nucleic acid templates suitable for use in such a reaction. For example, where whole genomic DNA is the target nucleic acid, it may be isolated from an organism, and fragmented to produce a population of template nucleic acids corresponding to the target nucleic acid. Further, target nucleic acid fragments or segments may be further subjected to size-selection (e.g., by chromatography, spin columns, or the like) to produce a pool of fragments within a desired size range (e.g., between about 500 and 5000 bp, or between about 700 and 2000 bp, or between about 500 and 20,000) or above a minimum size requirement, e.g., greater than about 250, 500, 1000, 2500, 5000, or 10,000 bp.

Isolation and/or purification of nucleic acids from samples is well known and routine in the art. Generally, nucleic acids can be extracted from a biological sample by a variety of techniques such as those described by Maniatis, et al., Molecular Cloning: A Laboratory Manual, Cold Spring Harbor, N.Y., pp. 280-281 (1982). A sample containing the target nucleic acid may be processed (e.g., homogenized or fractionated) in the presence of a detergent, surfactant, denaturant, reducing agent, and/or zwitterionic reagent by methods known in the art.

With reference to FIG. 1, the following is a description of certain aspects and embodiments of the preparations, compositions, methods, and systems presented herein. It is to be understood that this description is intended to be illustrative and not restrictive. It should be readily apparent to one skilled in the art that various embodiments and modifications may be made to this description without departing from the scope and spirit of the invention.

At step 1, the target nucleic acid may be optionally fragmented prior to addition of the primers. Such fragmentation may be carried out using generally understood laboratory techniques, e.g., using nebulization, sonication, restriction enzymes, nucleases, chemical cleavage, and the like. The fragments generated are typically 700-1000 bases (or base pairs) in length, however they may be longer or shorter depending on the specifics of the sequencing system used, e.g., the read length of the system. As noted above, the fragments can optionally be subjected to a size selection technique to produce a pool of fragments of a desired size range.

At step 2, the primers are added to the optionally fragmented target nucleic acid at a ratio of one (1) primer for every x bases, where x is typically from 12 to 200 bases (or base pairs) in the target nucleic acid, but may be longer or shorter depending on the specifics of the sequencing system used, e.g., the read length of the polymerase. Since the sequence of the target nucleic acid may not be known, the density of primer binding can be computed based on the average occurrence of a random primer of the length used. For example, if a nonomer is used, the average frequency of a complementary sequence is once in every $4^9$ (or 262,144) base pairs. So, if the density desired is one primer for every 200 bases, then ~1311 different nonomers must be annealed to the target nucleic acid (computed as $^{262,144}/_{200}$). In other embodiments in which the sequence of the target nucleic acid is known, nonrandom primers can be used and the primers can be designed to space the primers across the target nucleic acid or to localize the primers to specific locations on the target based on the sequence of the target nucleic acid, taking into account various aspects of primer design (e.g., GC content, melting temperature, hairpin formation, etc.). Primer design may be accomplished using various widely available primer design software applications, for example, Oligo® from Molecular Biology Insights (Cascade, Colo.). The ratio of primers to bases (or base pairs) of target nucleic acid may be further optimized for a given sample and sequencing system (e.g., instrument performance) by methods known to those of skill in the art.

At step 3, the target nucleic acid (and primers, if partially or completely double-stranded) is denatured. This denaturation may be performed by various methods known in the art, e.g., heat denaturation is one preferred method. Effective denaturation of nucleic acids occurs with high pH, low ionic strength, and/or heat, which disrupts base-pairing causing a double-stranded helix to dissociate into single strands. Any method that achieves essentially complete denaturation (e.g., >99.9%) of the nucleic acids and primers but does not interfere with the downstream steps of the method may be used. As such, to prevent such interference certain denaturation methods may require a purification step be performed to remove certain components of the denaturation reaction (e.g., urea, formamide, salt, etc.) prior to proceeding to a subsequent step in the process if these components would interfere with the subsequent step. An effective denaturation temperature may be computed by known methods base on various characteristics of a known nucleic acid, e.g., GC content and terminal nucleotides. Alternatively, heat denaturation of nucleic acids of unknown sequence typically uses a temperature high enough to ensure denaturation of even nucleic acids having a very high GC content, e.g., 95-98° C. in the absence of any chemical denaturant. It is well within the abilities of one of ordinary skill in the art to optimize the conditions (e.g., time, temperature, etc.) for denaturation of the target nucleic acid and primers.

At step 4, the primers are annealed to the target nucleic acid. This is generally accomplished by removal of the condition that caused the denaturation. For example, if the nucleic acids were heat denatured, then a cooling step will allow the primers to anneal to the target nucleic acid. This cooling step may optionally be performed by rapid cooling, which in some embodiments has been shown to increase efficiency for providing primable ends and a more homogeneous sample in terms of the size of the products of the annealing reaction, e.g., reducing inter-fragment hybridization. It is well within the abilities of one of ordinary skill in the art to optimize the conditions (e.g., time, temperature, buffer composition, etc.) for annealing of the target nucleic acid and primers and stabilization of the resulting target-primer complexes. Optionally, the target-primer complexes may be subjected to a size selection technique to remove any remaining unannealed primers and/or template nucleic acids outside of a desired size range, e.g., those less than 250-500 bp in length.

At step 5, polymerase is introduced and allowed to complex with the target-primer complexes. At step 6, the primers may be optionally pre-extended. In certain embodiments, such a pre-extension step can serve to stabilize the target nucleic acid/primer/polymerase complex prior to sequencing. In certain preferred embodiments, the pre-extension is performed at 0° C., but this temperature may be optimized by one of ordinary skill in the art based on, e.g., the polymerase used. In some embodiments, a nucleotide may be omitted from the pre-extension reaction to allow a hot start to be used for the subsequent sequencing reaction. For example, if thymine is omitted from the pre-extension reaction, the sequencing reaction may be hot-started on thymine, which has been found to be a highly efficient starting base. Alternatively, cytosine, guanine, or adenine may be omitted from the pre-extension and used as the starting base in the sequencing reaction. Finally, at step 7, single-molecule sequencing of the target nucleic acid is commenced, e.g., by addition of the base missing during the pre-extension reaction.

Another embodiment of the methods is shown in FIG. 2, in which pre-extension of the primers is not performed. Steps 1-4 are the same as those for FIG. 1, as described above. At step 5, the target nucleic acid and annealed primers are introduced and allowed to complex with polymerase, optionally subjected to size-selection, and the resulting target-primer-polymerase complexes are subjected to template-directed sequencing at step 6, as described below. A hot start, as described above, can also be used in the absence of pre-extension of the primer on the template. Further, various reaction conditions can be used to further control initiation of a template-directed sequencing reaction, either with or without pre-extension of the primer. For example, specific methods for controlling initiation and/or progression of primer extension including use of photoremovable blocking groups and divalent metal ions (e.g., $Mg^{2+}$, $Mn^{2+}$, and $Ca^{2+}$) are provided in U.S. Patent Publication No. 20080009007, U.S. Pat. No. 7,056,661, and U.S. patent application Ser. No. 12/414,191, filed Mar. 30, 2009, the disclosures of which are incorporated herein by reference in their entireties for all purposes. For a discussion of metal co-factor interaction in polymerase reactions, see, e.g., Arndt; et al., Biochemistry (2001) 40:5368-5375, which is also incorporated herein by reference in its entirety for all purposes. Immobilization of the polymerase/target nucleic acid complex can be performed before or after complex formation. For example, if the polymerase is to be immobilized during sequencing, the polymerase may be pre-immobilized prior to complex formation with the target-primer annealing product, or the target-primer-polymerase complexes may be pre-formed prior to immobilizing the polymerase in the sequencing system. Likewise, a target nucleic acid can be pre-immobilized, e.g. by hybridization to a complementary oligonucleotide at a reaction site, and subsequently contacted with primers and/or a polymerase enzyme.

Figure 3:
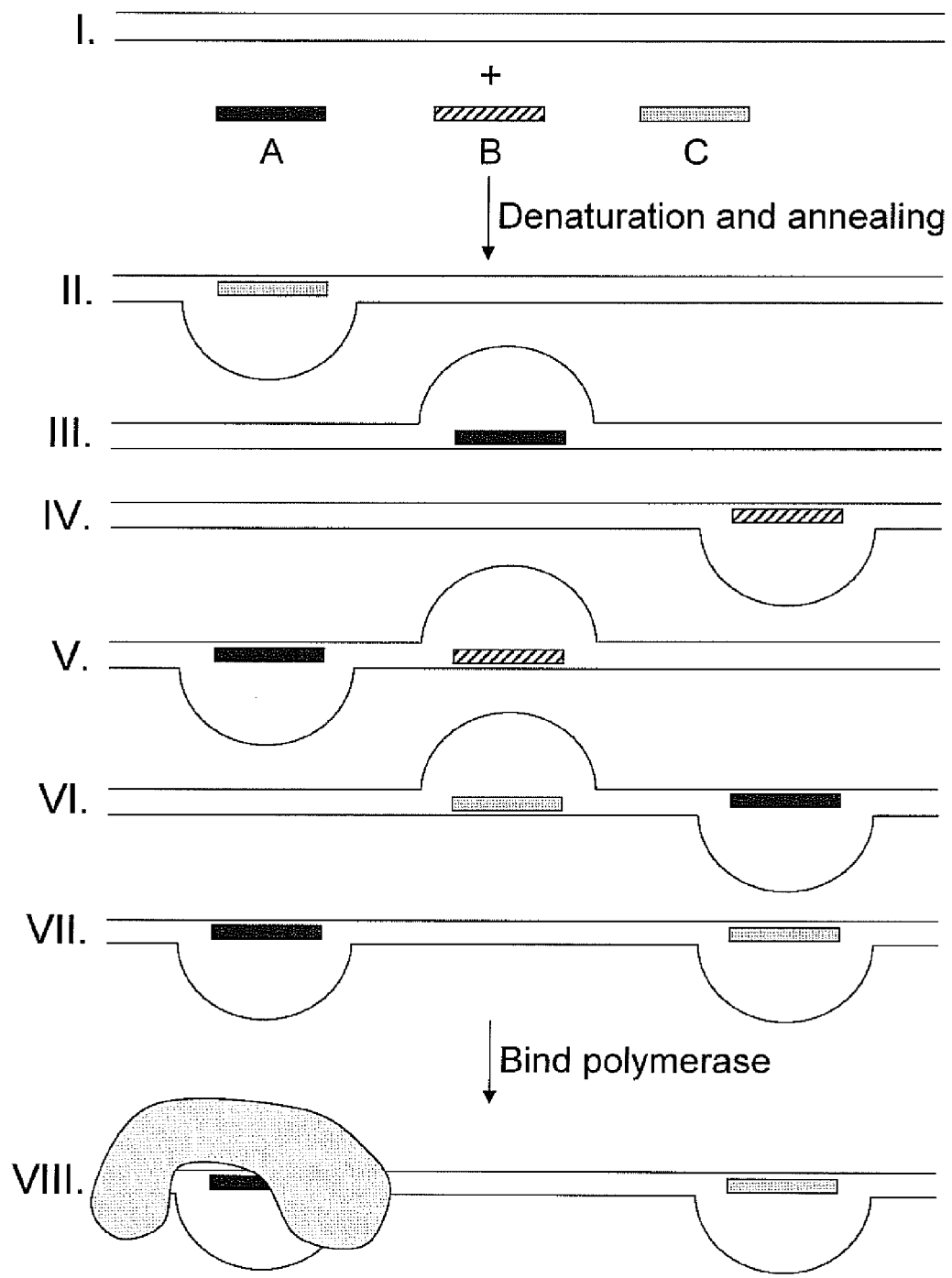
FIG. 3 illustrates an embodiment of the methods presented herein depicting polymerase binding to a target nucleic acid that is annealed to multiple different primers.

Since multiple primers are being annealed to a target nucleic acid preparation, some target nucleic acid molecules may anneal with multiple primers, as shown in FIG. 3. This illustrates a population of target nucleic acids (for simplicity, shown as one molecule I) and primers A, B, and C combined, denatured, and annealed. Resulting annealing products II, III, and IV all have only one primer annealed to them. Resulting annealing products V, VI, and VII each have two primers bound to a single target nucleic acid molecule. A polymerase added to the mixture would bind to a single location on a target nucleic acid where a primer has annealed, as shown as complex VIII. A polymerase with strand displacement activity to remove downstream primers is preferred in certain embodiments, as described below.

III. Sequencing of Target Nucleic Acids

At step 7 of FIG. 1 and step 6 of FIG. 2, sequencing of the target nucleic acid is initiated to begin synthesis of a nascent strand complementary to the strand of the target nucleic acid to which the primer serving as the polymerase initiation site is bound. These sequencing reactions are typically template-dependent, single-molecule sequencing reactions, as described below. In certain preferred embodiments, the sequencing reactions are monitored in real time, e.g., to detect incorporation of each base (or group of bases) into the growing nascent nucleic acid strand assembled processively by the polymerase.

Figure 4:
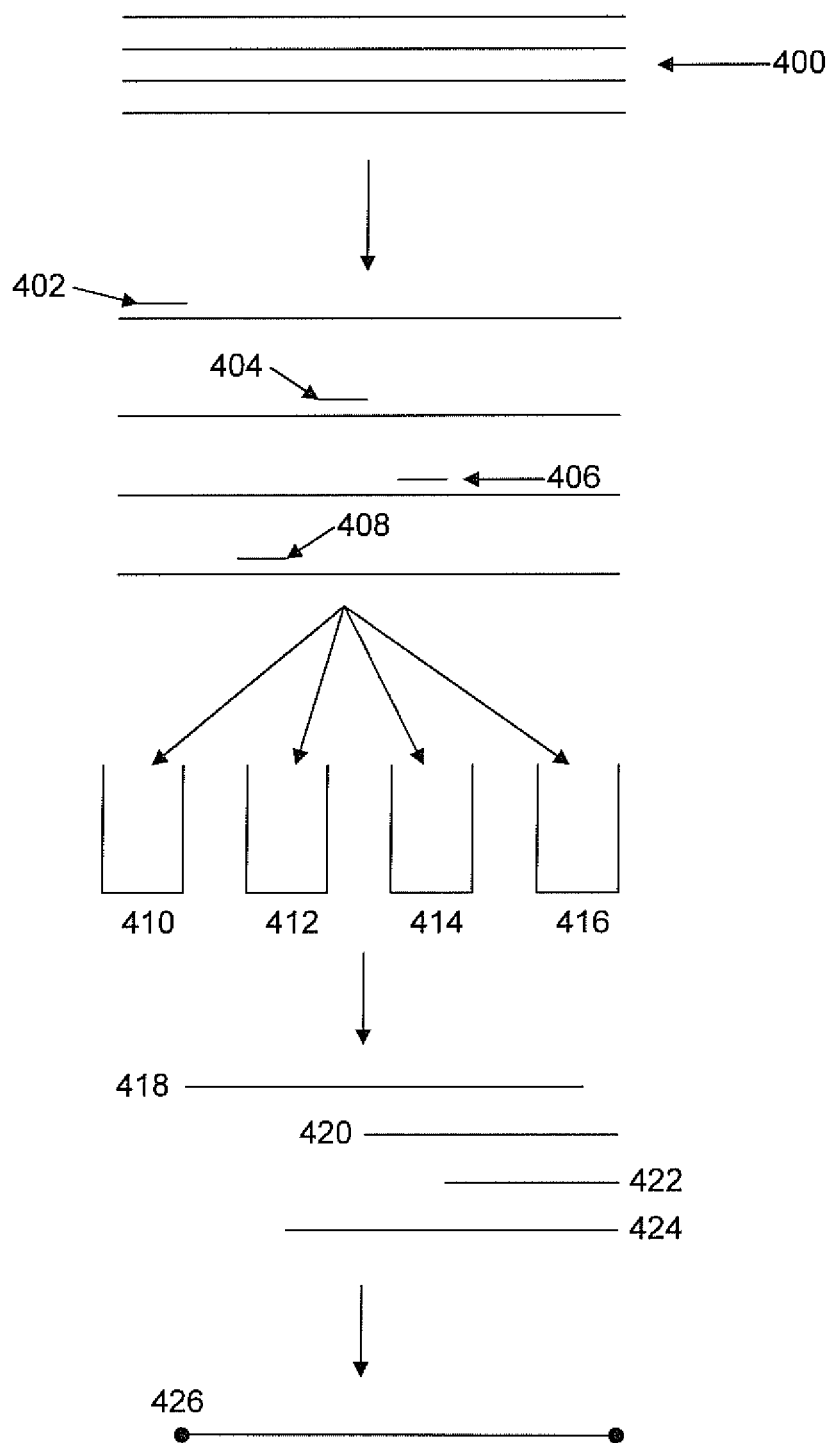
FIG. 4 provides a schematic illustration of the multiple priming processes of the invention.

FIG. 4 provides a simplified schematic illustration of one aspect of the invention. As shown, a population of identical large target nucleic acids, e.g., target nucleic acids 400, are provided. These large target nucleic acids may be amplification products, concatemeric nucleic acids, whole genomes, long chromosomal regions, plasmids, cosmids, viral genomes, or other large nucleic acids. Although illustrated as single-stranded target nucleic acids, it will be appreciated that the target nucleic acids can also be double-stranded or partially double-stranded. As such, primer annealing steps may require initial denaturation steps to provide opportunity for primer annealing. The target nucleic acids are contacted with multiple primers that are capable of priming multiple different locations in the target nucleic acids, e.g., primers 402, 404, 406 and 408.

The individual primed target nucleic acids are then subjected to separate single-molecule sequencing processes that monitor base-wise extension of each primer, shown as separate reactions 410-416. Although illustrated with a single primer hybridizing to each target nucleic acid 400, it will be appreciated that multiple primers will typically hybridize with each target nucleic acid. However, in the context of single-molecule sequencing processes that are preferred processes for use in conjunction with the invention, typically only a single primed location serves as a binding site for a polymerase and, therefore, only a single annealed primer is subjected to primer extension.

As shown, the multiple sequencing reactions, e.g., 410-416, provide multiple overlapping sequence reads from the population of template molecules, e.g., sequence reads 418-424. These overlapping sequence reads are then subjected to statistical analysis to provide a single consensus sequence 426 corresponding to the target nucleic acid 400, e.g., typically complementary to the strand of the target used as a template in the sequencing reactions. It will be appreciated that the use of double-stranded targets will additionally provide both sense and antisense fragments, whereupon sequence reads from such complementary fragments or fragment portions, may be subjected to statistical analysis to provide a consensus sequence for the target nucleic acid.

Figure 5:
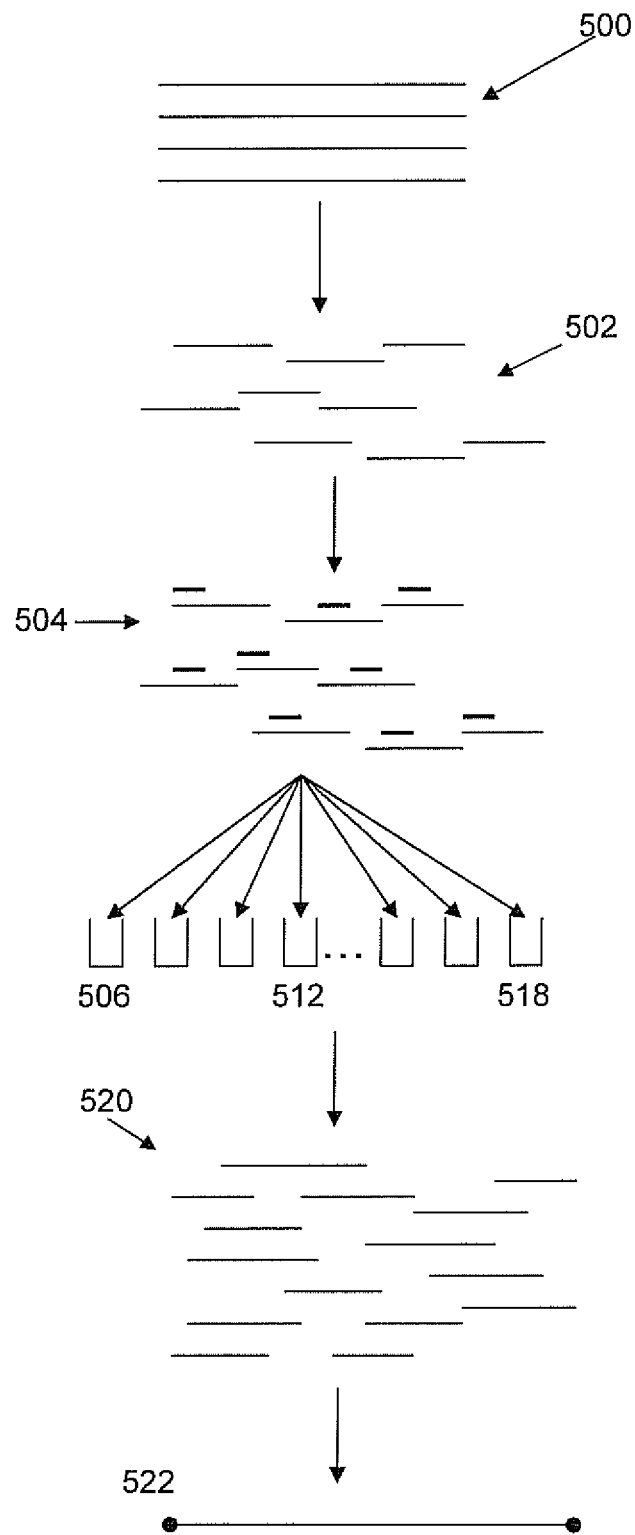
FIG. 5 provides a schematic illustration of an alternate multiple priming process of the invention in which the target nucleic acid is fragmented prior to priming.

Although illustrated in FIG. 4 as sequencing of intact large target nucleic acids, it will be appreciated that the target nucleic acid may additionally be fragmented prior to the multiple priming step set forth in FIG. 4. In particular, as shown in FIG. 5, a population of identical target nucleic acids 500 may be subject to fragmentation to provide a population of overlapping target nucleic acid fragments 502. The same multiple priming process is then employed to prime different portions of the target nucleic acid represented in the various different fragments, and each primed fragment 504, is then subjected to an individual sequencing process, e.g., as represented by reactions 506, 512 and 518. Again, although illustrated as a single primer for each fragment, it will be appreciated that multiple primers can associate with one or more fragments of the target nucleic acids. Optionally, as described elsewhere herein, size selection can be performed to remove target nucleic acid fragments of an undesired size and/or primers that do not anneal to a target fragment, e.g., using size exclusion spin columns. From the various sequencing reactions, a number of overlapping sequence reads derived from the differently primed target fragments 504 is obtained, and these overlapping sequence reads 520 are subjected to statistical analysis into a single continuous consensus sequence 522 corresponding to the starting sequence 500. Again, although shown as single-stranded targets and fragments, it will be appreciated that the target 500 and its fragments 502, may comprise double-stranded nucleic acids, as set forth above. Statistical analysis of sequence data to generate sequence information for a target nucleic acid is well known to those of ordinary skill in the art, and methods particularly applicable to the invention are provided, e.g., in U.S. Patent Publication No. 20090024331, the disclosure of which is incorporated herein by reference in its entirety for all purposes. Methods for generating consensus sequence from multiple sequence reads are known in the art and certain specific embodiments are provided in U.S. Ser. No. 61/116,439, filed Nov. 20, 2008, the disclosure of which is incorporated herein by reference in its entirety for all purposes.

Nucleotides

In another aspect, the nucleotides or nucleotide analogs used in the sequencing reaction (or in primer composition) or may be naturally-occurring or synthetic, and may include polynucleotide mimetics, e.g., methylated nucleic acids, peptide nucleic acids, modified peptide nucleic acids, locked nucleic acids, and any other structural moiety that can act substantially like a nucleotide or base, for example, by exhibiting base-complementarity with one or more bases that occur in DNA or RNA, and/or being capable of base-complementarity incorporation. In some embodiments, sequencing reactions for use with the methods presented herein include nucleotides that are tagged with a detectable label that is directly or indirectly detectable. Such detectable labels can include, for example, optically-detectable labels such as fluorescent labels, including but not limited to 4-acetamido-4'-isothiocyanatostilbene-2,2' disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144;

IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Ciba-cron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. In particularly preferred sequencing processes, nucleotide analogs are employed that include optically detectable labeling groups that are released upon incorporation of the nucleotide into an extended primer during polymerase mediated synthesis. Examples of preferred compounds include, e.g., terminal phosphate labeled nucleotides, e.g., as described in U.S. Pat. Nos. 6,399,335, 7,056,661, 7,052,847, 7,033,764, 7,056,676, 7,361,466, 7,416,844, 6,936,702, and 7,041,812, the full disclosures of which are incorporated herein by reference in their entirety for all purposes.

Labels other than fluorescent labels are contemplated by the invention, including other optically-detectable labels. In addition to the foregoing optical labels, other optically detectable labeling groups, moieties or structures are also optionally included upon the nucleotide analogs used in conjunction with the invention. For example, semiconductor nanocrystals, also termed "quantum dots," that possess fluorescent properties may be employed as the optically detectable labeling groups. Such materials are described in, e.g., U.S. Pat. Nos. 6,426,513, 6,855,551, and 6,207,392, the full disclosures of which are incorporated herein by reference in their entirety for all purposes.

For example, in certain embodiments of the invention, the nucleotides incorporated into the nascent strand during sequencing are fluorescently labeled. In some such embodiments, a polymerase synthesizes the complement to the target nucleic acid using four different fluorescent dNTP analogs. Subsequently, an exonuclease is added to sequentially release the individual fluorescently labeled bases incorporated by the polymerase. (See, e.g., Goodwin et al., "Application of Single Molecule Detection to DNA Sequencing." *Nucleos. Nucleot.* 16: 543-550 (1997).) The individual released bases are detected, e.g., in a hydrodynamic flow detector or an ultrasensitive fluorescence spectrometer, and the sequence of the target nucleic acid is determined based on complementarity with the nascent strand degraded by the exonuclease. In other embodiments, a set of identical single-stranded DNA molecules are linked to a substrate and the sequence is determined by repeating a series of reactions using fluorescently labeled dNTPs. (See, e.g., U.S. Pat. No. 5,302,509.) This method requires that each base also contains a 3'-dNTP blocking group, and after the addition and detection of the base, the fluorescent label and blocking group must be removed prior to addition of the next base in the nascent strand.

Polymerases

Various polymerases may be used in the methods described herein, including DNA polymerases, RNA polymerases, reverse transcriptases, and mutant or altered forms of any of the foregoing. DNA polymerases and their properties are described in detail in, among other places, DNA Replication $2^{nd}$ Edition, Kornberg and Baker, W.H. Freeman, New York, N.Y. (1991). Known conventional DNA polymerases useful in the invention include, but are not limited to, *Pyrococcus furiosus* (Pfu) DNA polymerase (Lundberg et al., 1991, Gene, 108: 1, Stratagene), *Pyrococcus woesei* (Pwo) DNA polymerase (Hinnisdaels et al., 1996, Biotechniques, 20:186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475: 32), *Thermococcus litoralis* (Tli) DNA polymerase (also referred to as Vent™ DNA polymerase, Cariello et al., 1991, Polynucleotides Res, 19: 4193, New England Biolabs), 9.degree. Nm™ DNA polymerase (New England Biolabs), Stoffel fragment, ThermoSequenase® (Amersham Pharmacia Biotech UK), Therminator™ (New England Biolabs), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteoriol, 127: 1550), DNA polymerase, *Pyrococcus kodakaraensis* KOD DNA polymerase (Takagi et al., 1997, Appl. Environ. Microbial. 63:4504), JDF-3 DNA polymerase (from *thermococcus* sp. JDF-3, Patent application WO 0132887), *Pyrococcus* GB-D (PGB-D) DNA polymerase (also referred as Deep Vent™ DNA polymerase, Juncosa-Ginesta et al., 1994, Biotechniques, 16:820, New England Biolabs), UlTma DNA polymerase (from thermophile *Thermotoga maritima*; Diaz and Sabino, 1998 Braz J. Med. Res, 31:1239; PE Applied Biosystems), Tgo DNA polymerase (from *thermococcus gorgonarius*, Roche Molecular Biochemicals), *E. coli* DNA polymerase I (Lecomte and Doubleday, 1983, Polynucleotides Res. 11:7505), T7 DNA polymerase (Nordstrom et al., 1981, J. Biol. Chem. 256:3112), and archaeal DP11/DP2 DNA polymerase II (Cann et al., 1998, Proc Natl Acad. Sci. USA 95:14250→5).

While mesophilic polymerases are contemplated by the invention, certain preferred polymerases are thermophilic. Thermophilic DNA polymerases include, but are not limited to, ThermoSequenase®, 9.degree. Nm™, Therminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof.

Reverse transcriptases useful in the invention include, but are not limited to, reverse transcriptases from HIV, HTLV-1, HTLV-II, FeLV, FIV, SIV, AMV, MMTV, MoMuLV and other retroviruses (see Levin, Cell 88:5-8 (1997); Verma, Biochim Biophys Acta. 473:1-38 (1977); Wu et al., CRC Crit Rev Biochem. 3:289-347 (1975)).

In preferred embodiments, the polymerases employed during the sequencing processes, and optionally during pre-sequencing synthesis, will typically possess strand-displacement activity to displace any primers downstream of the primer at which the strand synthesis is initiated. A preferred rolling circle polymerase exhibits strand-displacement activity, and as such, a single circular template can be sequenced repeatedly to produce a sequence read comprising multiple copies of the complement of the template strand by displacing the nascent strand ahead of the translocating polymerase. Non-limiting examples of rolling circle polymerases suitable for the present invention include but are not limited to T5 DNA polymerase, T4 DNA polymerase holoenzyme, phage M2 DNA polymerase, phage PRD1 DNA polymerase, Klenow fragment of DNA polymerase, and certain polymerases that are modified or unmodified and chosen or derived from the phages Φ29, PRD1, Cp-1, Cp-5, Cp-7, Φ15, Φ1, Φ21, Φ25, BS 32 L17, PZE, PZA, Nf, M2Y (or M2), PR4, PR5, PR722, B103, SF5, GA-1, and related members of the Podoviridae family. In certain preferred embodiments, the polymerase is a modified Phi29 DNA polymerase, e.g., as described in U.S. Patent Publication No. 20080108082, incorporated herein by reference in its entirety for all purposes. Similarly, polymerases having enhanced activity for labeled nucleotides are also desirable. Examples of polymerase enzymes for use in various aspects of the invention include, e.g., those described in U.S. patent application Ser. No. 11/645,125, filed Dec. 21, 2006; Ser. No. 11/645,135, filed Dec. 21, 2006; Ser. No. 12/384,112, filed Mar. 30, 2009; 61/094,843, filed Sep. 5, 2008; and 61/072,645, filed Mar. 31, 2008; as well as U.S. Patent Publication No. 20070196846 (the full disclosures of which are incorporated herein by reference in their entireties for all purposes), such as the E375Y/K512Y/T368F mutant polymerase described in the foregoing.

In certain preferred embodiments, the polymerases used in the methods herein are highly processive and able to generate long sequence reads in the sequence-by-synthesis reactions described herein. For example, a polymerase used in the methods herein is typically capable of incorporating at least about 50, 75, 100, 250, 500, 1000, 2500, 5000, or at least 10,000 nucleotides into a single nascent strand. Polymerase enzymes, and in particular replicative polymerases, with long readlength capabilities are included in those provided above, e.g., Φ29, and others are known to those of ordinary skill in the art.

Substrates

As described previously, in certain preferred aspects, single-molecule real-time sequencing processes are used in conjunction with the invention. In such processes, one typically benefits from the optical isolation or confinement of the reaction complex, in order to maximally observe the addition of individual nucleotides. While a variety of methods are available to optically confine these reaction complexes, e.g., through spatial isolation of complexes and/or the use of total internal reflectance microscopy, i.e., to illuminate only those species provided at or near the surface of a transparent substrate, in particularly preferred systems, optical confinement is provided through the use of zero mode waveguide (ZMW) arrays, where individual complexes are provided disposed within an observation volume of the ZMWs. The fabrication and application of ZMWs in biochemical analysis is described, e.g., in U.S. Pat. Nos. 6,917,726, 7,013,054, 7,181,122, and 7,292,742, the full disclosures of which are incorporated herein by reference in their entirety for all purposes.

Briefly, ZMWs typically comprise a transparent substrate layer, e.g., glass, quartz, etc., upon which is disposed an opaque, typically metal, cladding layer. Apertures with cross-sectional dimensions on the order of 10 to 250 nanometers are disposed through the cladding layer to the underlying substrate to provide a core of the ZMW. Because their cross-sectional dimensions are in the nanoscale range, these apertures do not allow for the propagation of light that exceeds a cutoff frequency that is a function of such cross-sectional dimension. Direction of such light at an open end of the core, e.g., through the transparent substrate, will result in an illumination volume within the core that corresponds to the evanescent field that decays exponentially with the distance into the core. As a result, only a very small volume at the base of the core is subjected to illumination sufficient to observe reaction components, and this small volume is typically referred to as the "observation volume" or "illumination volume." By placing the synthesis complex within that volume, and utilizing fluorescent nucleotide analogs, one can readily identify when a nucleotide is retained by the complex for incorporation into a nascent strand, while excluding illumination of other unincorporated nucleotides, e.g., those in solution outside of the observation volume. The fluorescent signals from incorporation events are detected and used to identify which bases were incorporated and in what order.

Detection

Any detection method may be used that is suitable for the type of label and the sequencing process employed. Thus, exemplary detection methods include radioactive detection, optical absorbance detection, e.g., UV-visible absorbance detection, optical emission detection, e.g., fluorescence or chemiluminescence. For example, nucleotide incorporation can be detected on a substrate by scanning all or portions of each reaction site on the substrate simultaneously or serially, depending on the scanning method used, to detect changes in signal indicative of the incorporation of a particular nucleotide or nucleotide analog to the nascent nucleic acid strand. For fluorescence labeling, selected regions on a substrate may be serially scanned one-by-one or row-by-row using a fluorescence microscope apparatus, such as described in Fodor (U.S. Pat. No. 5,445,934) and Mathies et al. (U.S. Pat. No. 5,091,652). Devices capable of sensing fluorescence from a single molecule include scanning tunneling microscope (siM) and the atomic force microscope (AFM). Hybridization patterns may also be scanned using a CCD camera (e.g., Model TE/CCD512SF, Princeton Instruments, Trenton, N.J.) with suitable optics (Ploem, in Fluorescent and Luminescent Probes for Biological Activity Mason, T. G. Ed., Academic Press, Landon, pp. 1-11 (1993), such as described in Yershov et al., Proc. Natl. Aca. Sci. 93:4913 (1996), or may be imaged by TV monitoring. For radioactive signals, a phosphorimager device can be used (Johnston et al., Electrophoresis, 13:566, 1990; Drmanac et al., Electrophoresis, 13:566, 1992; 1993). Other commercial suppliers of imaging instruments include General Scanning Inc., (Watertown, Mass. on the World Wide Web at genscan.com), Genix Technologies (Waterloo, Ontario, Canada; on the World Wide Web at confocal.com), and Applied Precision Inc. Preferred detection methods achieve simultaneous scanning of multiple target nucleic acids, e.g., simultaneous scanning of all polymerase reactions taking place on individual target nucleic acids immobilized, directly or indirectly, on a substrate. In certain preferred embodiments, hundreds or thousands of nucleic acids are monitored simultaneously on a single substrate.

A number of approaches can be used to detect incorporation of fluorescently-labeled nucleotides into a single nucleic acid molecule. Optical setups include near-field scanning microscopy, far-field confocal microscopy, wide-field epi-illumination, light scattering, dark field microscopy, photoconversion, single and/or multiphoton excitation, spectral wavelength discrimination, fluorophore identification, evanescent wave illumination, and total internal reflection fluorescence (TIRF) microscopy. In general, certain methods involve detection of laser-activated fluorescence using a microscope equipped with a camera. Suitable photon detection systems include, but are not limited to, photodiodes and intensified CCD cameras. For example, an intensified charge couple device (ICCD) camera can be used. The use of an ICCD camera to image individual fluorescent dye molecules in a fluid near a surface provides numerous advantages. For example, with an ICCD optical setup, it is possible to acquire a sequence of images (movies) of fluorophores. Particularly preferred processes employed systems for detection of incorporation events from such substrates as described in, e.g., U.S. Patent Application No. 2007-0188750, and published International Patent Application No. WO 2007/019582, the full disclosures of which are incorporated herein by reference in their entireties for all purposes.

Some embodiments of the present invention use TIRF microscopy for two-dimensional imaging. TIRF microscopy uses totally internally reflected excitation light and is well known in the art. See, e.g., the World Wide Web at nikoninstruments.jp/eng/page/products/tirf.aspx. In certain embodiments, detection is carried out using evanescent wave illumination and total internal reflection fluorescence microscopy. An evanescent light field can be set up at the surface, for example, to image fluorescently-labeled nucleic acid molecules. When a laser beam is totally reflected at the interface between a liquid and a solid substrate (e.g., a glass), the excitation light beam penetrates only a short distance into the liquid. The optical field does not end abruptly at the reflective interface, but its intensity falls off exponentially with distance. This surface electromagnetic field, called the "evanescent wave", can selectively excite fluorescent molecules in the liquid near the interface. The thin evanescent optical field at the interface provides low background and facilitates the detection of single molecules with high signal-to-noise ratio at visible wavelengths.

The evanescent field also can image fluorescently-labeled nucleotides upon their incorporation into the attached template/primer complex in the presence of a polymerase. Total internal reflectance fluorescence microscopy is then used to visualize the attached template/primer duplex and/or the incorporated nucleotides with single molecule resolution.

III. Strand Displacement

As noted previously, each molecule of target nucleic acid is likely to have more than one primer annealed to it during sequencing, although only one will be used as a synthesis start site, e.g., as shown in FIG. 3. As will be appreciated, in such cases, it will be preferable to remove the additional primers either prior to or during the template-dependent sequencing process. In the case of, for example, sequence-by-incorporation processes, strand separation is preferably carried out through the selection and use of a strand-displacing polymerase enzyme. A variety of strand-displacing polymerase enzymes are known in the art, including, for example, Φ29 polymerase and Φ29-type polymerases (See, e.g., U.S. Pat. Nos. 5,001,050, 5,576,204, the full disclosures of which are incorporated herein by reference in their entirety for all purposes), Bst Polymerase (available from New England Biolabs), as well as those polymerases described in commonly owned International Patent Application Nos. WO 2007/075987, WO 2007/075873, WO 2007/076057 the full disclosures of which are incorporated herein by reference in their entirety for all purposes.

In certain preferred embodiments, the target nucleic acid is a single-stranded circular nucleic acid that is complexed with one or more primers and a strand-displacing polymerase, and contacted with the four nucleotides, or in the case of certain preferred aspects, fluorescently labeled nucleotide analogs. Upon complete synthesis, e.g., one full cycle around the template, a double-stranded circular nucleic acid results, made up of the original template and the newly synthesized or nascent strand. As synthesis progresses, the polymerase displaces the complementary nascent strand from the strand bound by the polymerase and synthesis of the nascent strand continues. Since the strand-displacing polymerase enzyme can continue to displace the complementary strand, e.g., the newly synthesized nascent strand, the synthesis, and by implication, the sequencing process can continue through the template multiple times to provide multiple sequence reads of the template for use in further statistical analysis, e.g., variant detection and/or consensus sequence determination.

Figure 6:
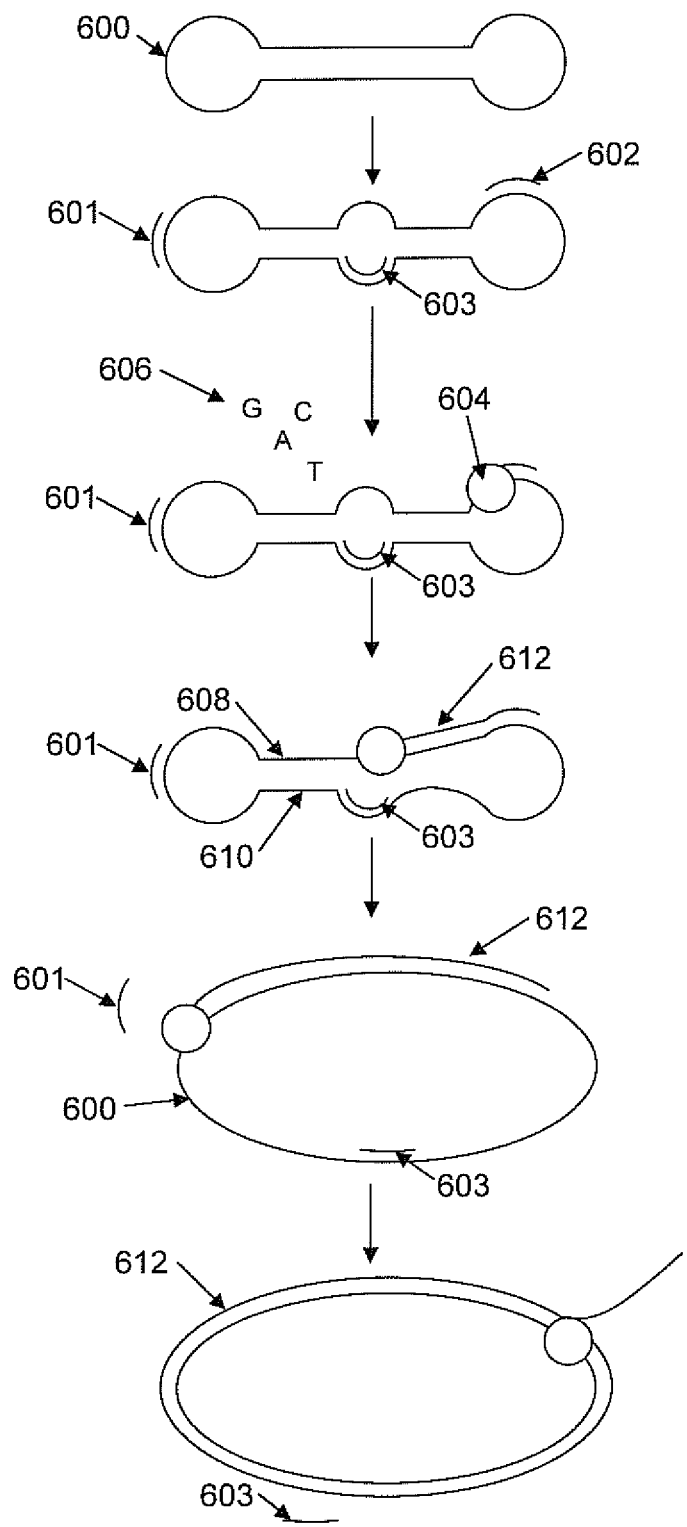
FIG. 6 provides an illustrative embodiment in which a template nucleic acid comprises both double-stranded and single-stranded regions, where the double-stranded regions comprise regions of internal complementarity between two different segments of a circular single-stranded nucleic acid.

FIG. 6 depicts an embodiment in which the template nucleic acid comprises both double-stranded and single-stranded regions, where the double-stranded regions comprise regions of internal complementarity between two different segments (608 and 610) of a circular single-stranded nucleic acid 600. Methods for making and using such templates, e.g., in nucleic acid sequencing applications, are provided in U.S. Ser. No. 61/072,160, filed Mar. 28, 2008; U.S. Ser. No. 61/099,696, filed Sep. 24, 2008; U.S. Ser. No. 12/383,855, filed Mar. 27, 2009; and U.S. Ser. No. 12/413,258, filed Mar. 27, 2009, the disclosures of which are incorporated herein by reference in their entireties for all purposes. As shown, the target nucleic acid template 600 is complexed with three primers 601, 602, and 603, and a strand-displacing polymerase 604. Nucleotides 606 present in the reaction mixture are used by the polymerase 604 to synthesize a nascent nucleic acid strand 612 complementary to the template 600. As synthesis continues, the polymerase displaces one complementary segment 608 from the other complementary segment 610 and synthesis of the nascent strand 612 continues. Further, primers 601 and 603, which were not used by the polymerase to initiate synthesis, are also displaced by the translocating polymerase. Upon completion of one round of synthesis around the template, a double-stranded template results comprising the original template 600 and the newly synthesized strand 612. The strand-displacing polymerase continues to add nucleotides to the 3' end of strand 612 by displacing the primer and the 5' end of strand 612 ahead of the polymerase as it proceeds around the template 600. In this way, the polymerase can proceed around the template multiple times, thereby generating a concatemeric nascent strand comprising multiple copies of the complement to the original template nucleic acid. Although depicted with only three primers, the template can be annealed to even more primers, bound to a single polymerase complex, and after initiation of synthesis from one of the bound primers the strand-displacing activity of the polymerase will allow synthesis to continue by displacing any other primers bound to the substrate, as shown for primers 601 and 603.

Alternatively, other mechanisms may be employed to affect strand separation prior to or during synthesis. For example, elevation of the temperature of the reaction mixture may be used to facilitate binding of primers to double-stranded regions of a template. As will be appreciated, primers, as well as additional portions of the linking oligo-nucleotides, may be employed that have relatively higher melting temperatures than an average, naturally occurring nucleic acid, e.g., those comprising GC-rich sequences. Other methods for promoting strand separation, such as addition of certain denaturants, are known to those of ordinary skill in the art. In certain embodiments, once the double-stranded segment is duplicated to a sufficient degree to prevent re-hybridization of the original template, by virtue of the presence of the nascent strand, there is no longer a need for denaturation steps or additives.

Further, during the synthesis reaction, elevation of the temperature can be used to melt the double-stranded portion of the template or regions at which additional primers are bound, and permit primer extension through those regions, e.g., when polymerases that are not capable of strand displacement are used. As will be appreciated, for such applications in which elevated temperatures are used during synthesis, it may be desirable to employ thermally stable polymerase enzymes that are better suited to the temperatures required for melting and continued synthesis. A wide variety of thermostable polymerases are known in the art and are applicable to this type of application, including, for example Taq polymerase and its variants. As will also be appreciated, in the case of the use of non-strand-displacing enzymes, additional strand separation steps will typically be needed following one complete cycle around the template, as the nascent strand would then be in position to block continued synthesis. The requirement for a triggering event, e.g., an elevation in temperature to allow synthesis to initiate or proceed, can provide advantages of synchronizing different steps in the template sequencing process. For example, if the temperature is lower than the melting temperature of the 5' end of the nascent strand, synthesis will stop when the polymerase has completed one copy of the template, and can be reinitiated as the investigator's discretion, e.g., to synchronize a set of sequencing reactions being carried out simultaneously. Alternatively, the synthesis reaction comprising a thermally stable polymerase may be maintained at elevated temperatures to ensure continuous, uninterrupted synthesis and sequencing. Alternatively or additionally, primers can be modified such that they can be displaced from the template by a translocating polymerase enzyme that exhibits poor or no strand displacement activity on primers not so modified. In certain embodiments, primers can comprise modified nucleotides that favor a lower degree of stacking, and therefore a lower stability of the resulting primer:template duplex. In certain embodiments, primers can be designed to comprise a 5' portion or "tail" that does not hybridize with the template nucleic acid. During initiation, a polymerase binds the hybridized 3' end of a single primer annealed to the template and commences primer extension by nucleotide incorporation. Additional primers bound to the template will be approached by the polymerase from the 5' end, and the presence of the unhybridized portion will facilitate displacement of the primer. Similarly, the annealed primer can comprise modified nucleotides that have a sufficiently high affinity for the template to allow binding under a first set of reaction conditions, but that have a low affinity for the template under a second set of reaction conditions. For example, primer extension is initiated at the first set of reaction conditions, and subsequently the reaction conditions are changed, e.g., by changing the salt concentration, to promote displacement of primers ahead of the translocating polymerase. Further, for a polymerase that has a condition-dependent strand displacement activity, the progression of the reaction can be controlled by changing the conditions from permissive to restrictive, and vice versa, e.g., by changing cofactors or other conditions in the reaction mixture. In certain preferred embodiments, the polymerase translocates around the template multiple times, thereby generating a concatemeric nascent nucleic acid product whose synthesis can be monitored to provide multiple sequence reads of the template nucleic acid.

Figure 7:
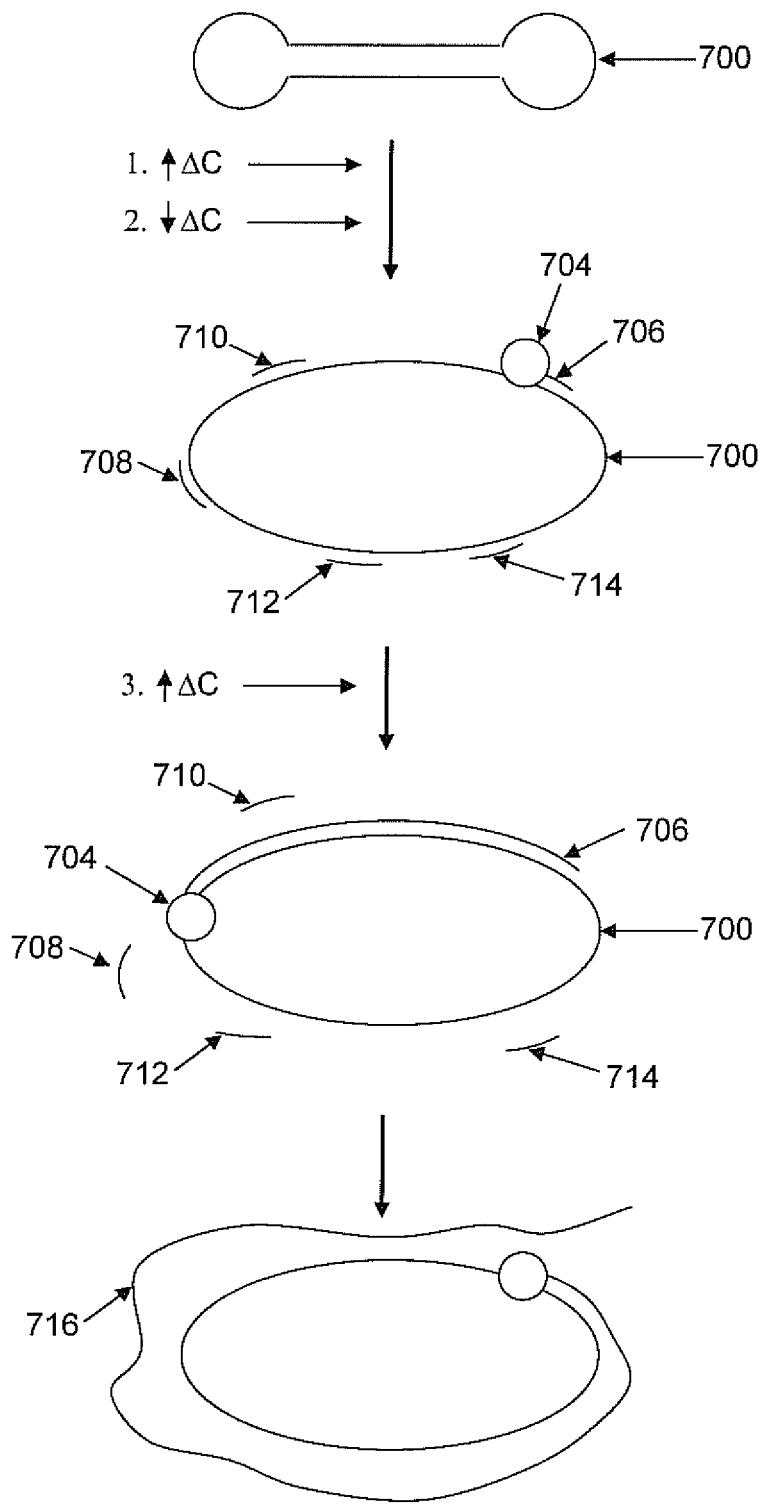
FIG. 7 provides an illustrative schematic of synthesis using a thermally regulated process and a thermostable polymerase that is not capable of strand-displacement.

A schematic of synthesis using a thermally regulated process and a thermostable polymerase that is not capable of strand-displacement is illustrated in FIG. 7. As shown, template 700 comprises a double-stranded region and two single-stranded regions. The template 700 is heat-denatured e.g., through heating sufficient to melt the double-stranded segment (indicated as AC), and subsequently the temperature is lowered to allow hybridization of primers 706, 708, 710, 712, and 714 to bind template 700. The primer-template complex is contacted with a thermostable polymerase enzyme 704, which binds to the template at primer 706. The polymerase commences synthesis of a nascent strand complementary to template 700, but is unable to displace other primers bound to the template at the lower temperature so synthesis cannot readily proceed if an annealed primer is subsequently encountered. As such, the temperature is elevated once again, this time to remove primers at locations on the template that are not bound by the polymerase, e.g., primers 710, 708, 712, and 714. The elevated temperature during synthesis must occur after the polymerase has bound at an annealed primer, and can optionally occur after a pre-extension of the primer, as described elsewhere herein. Further, the elevated temperature can serve to displace the nascent strand 716 as shown in FIG. 7, thereby allowing the thermostable polymerase to continue processing the template even after a full-length complementary strand has been generated. As will be clear to one of ordinary skill, such a strategy is also appropriate for a single-stranded circular template that does not have internal complementarity, and that in such an implementation the initial temperature elevation (1.) would not be required to denature a double-stranded portion, but the subsequent temperature elevation (3.) would still be required to remove the primers ahead of the polymerase.

IV. Software and Algorithm Implementations

The methods herein may operate with various different methods for performing statistical analysis on nucleotide sequence read data. Such methods are known to those of ordinary skill in the art and widely available in the literature. For example, the methods herein may operate with numerous methods for sequence alignment including those generated by various types of known multiple sequence alignment (MSA) algorithms. For example, the sequence alignment may comprise one or more MSA algorithm-derived alignments that align each read using a reference sequence. In some embodiments in which a reference sequence is known for the region containing the target sequence, the reference sequence can be used to produce an MSA using a variant of the center-star algorithm. Alternatively, the sequence alignment may comprise one or more MSA algorithm-derived alignments that align each read relative to every other read without using a reference sequence ("de novo assembly routines"), e.g., PHRAP, CAP, ClustalW, T-Coffee, AMOS make-consensus, or other dynamic programming MSAs. Depending on the sequence-generating methods used, the determination of sequence alignment may also involve analysis of read quality (e.g., using TraceTuner™, Phred, etc.), signal intensity, peak data (e.g., height, width, proximity to neighboring peak(s), etc.), information indicative of the orientation of the read (e.g., 5'→3' designations), clear range identifiers indicative of the usable range of calls in the sequence, and the like. Additional algorithms and systems for statistical analysis of nucleotide sequence read data, e.g., sequence alignment, are well know to those of skill in the art, and are described further, e.g., in G. A. Churchill, M. S. Waterman (1992) "The Accuracy of DNA Sequences: Estimating Sequence Quality," *Genomics* 14: 89-98; M. Stephens, et al. (2006) "Automating sequence-based detection and genotyping of SNPs from diploid samples," *Nat. Genet.*, 38: 375-381; J. Hein (1989) *Mol. Biol. Evol.*, 6: 649-668; U.S. Ser. No. 12/134,186, filed Jun. 5, 2008; and U.S. Ser. No. 61/116,439, filed Nov. 20, 2008.

The software and algorithm implementations for statistical analysis of sequence reads generated by the methods of the invention are preferably machine-implemented methods, and are preferably performed via a user interface implemented in a machine that comprises instructions stored in machine-readable medium and a processor that executes the instructions. The results of these methods are preferably stored on a machine-readable medium, as well. Further, the invention provides a computer program product comprising a computer usable medium having a computer readable program code embodied therein, the computer readable program code adapted to implement one or more of the methods described herein, and optionally also providing storage for the results of the methods of the invention.

In another aspect, the invention provides data processing systems for transforming sequence read data from one or more sequencing reactions into consensus sequence data representative of an actual sequence of one or more template or target nucleic acids analyzed in the one or more sequencing reactions. Such data processing systems typically comprise a computer processor for processing the sequence read data according to the steps and methods described herein, and computer usable medium for storage of the initial sequence read data and/or the results of one or more steps of the transformation (e.g., the consensus sequence data).

It is to be understood that the above description is intended to be illustrative and not restrictive. It readily should be apparent to one skilled in the art that various embodiments and modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated by reference in its entirety for all purposes.

IX. Examples

The preparations, compositions, methods, and systems described herein were employed in various sequencing applications which are described in greater detail, below.

Example I

Sequencing of phiX174 Genome

The genome of the phiX174 bacteriophage is a covalently closed circle of single-stranded DNA, and was the first DNA-based genome to be sequenced by Fred Sanger and his team in 1977. This phage has a small genome with 11 genes in 5386 bases.

The single-stranded virion form of the genome was sequenced in one embodiment of the invention described herein as follows. First, the genome was heated to 95° C. in the presence of 106 primers that were designed based on the known sequence of phiX174. The primers were each 12 bases in length and were designed to anneal to the phiX174 genomic sequence with a spacing of about one primer every 50 bases of genomic DNA, and to anneal to the target just 3' of an A in the target nucleic acid (so that the first incorporated base is a T).

Annealing was accomplished by a slow-cool process to prime the genome for template-directed sequencing. The stoichiometry of the annealing was 1:1, with 200 nM of each primer and 200 nM of the phiX174 DNA. The annealing buffer contained 50 mM MOPS, pH 7.5, and 150 mM potassium acetate.

Figure 8:
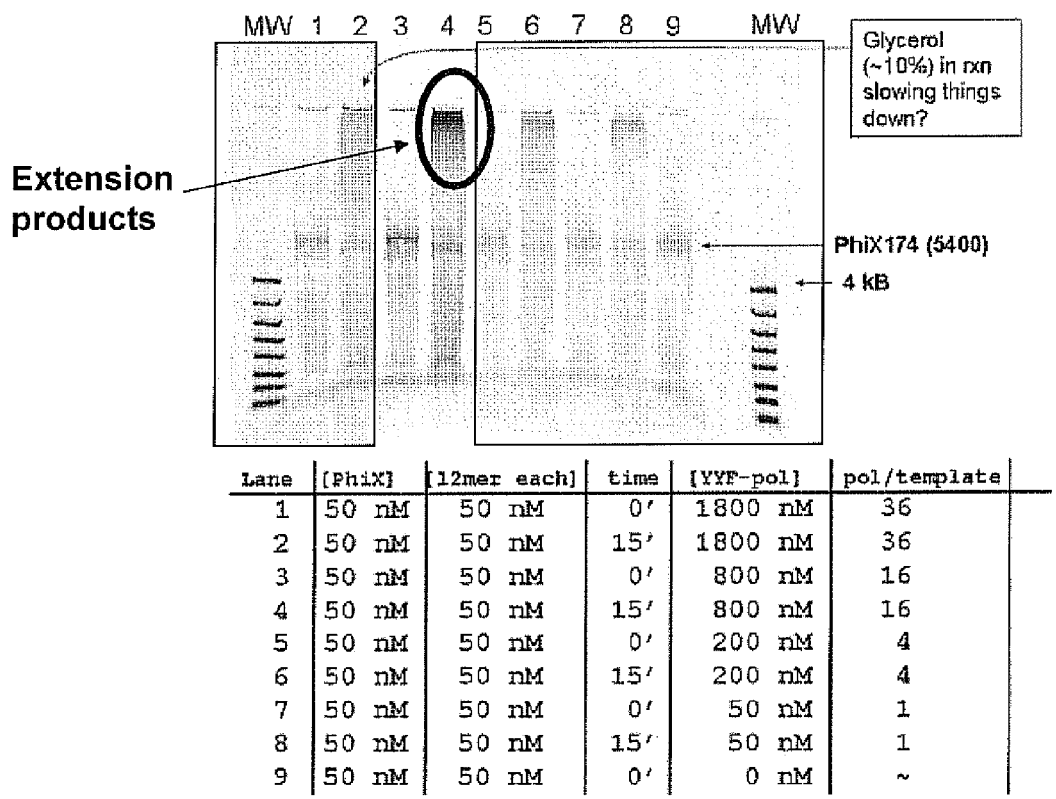
FIG. 8 provides analysis of extension products from multiply primed template nucleic acids.

To first test whether the polymerase would extend the primed phiX174 DNA, extension reactions were performed by first diluting the primed template to 50 nM in reaction buffer (50 mM MOPS, pH 7.5; 150 mM potassium acetate; 5 mM DTT; 100 µM dATP, dCTP, dGTP; 25 µM ALEXA488-Chromatide dUTP (Invitrogen); 75 µM dTTP; and 1 mM MnCl2. The polymerase concentration was varied from 50 nM to 1800 nM as indicated in FIG. 8. The polymerase employed was a highly processive, strand-displacing DNA polymerase that was exonuclease-deficient (See, e.g., Published U.S. Patent Application No. 2007-0196846 and 61/072,645, filed Mar. 31, 2005, the full disclosures of which are incorporated herein by reference in their entirety for all purposes). Reactions were performed for 15 minutes at room temperature. The reactions were quenched by addition of EDTA to final concentration of 50 mM. Extension products were analyzed by electrophoresis on a 0.7% agarose gel (FIG. 8). Extension products were identified by incorporation of the ALEXA488-chromatide into large molecular weight DNA products as imaged on a Typhoon (GE/Amersham). These data demonstrated that the pooled primed phiX174 DNA does extend in bulk.

To test the direct-primed template in ZMW sequencing, a polymerase enzyme was added to the template-primer complex in a solution of 50 mM MOPS pH 7.5, 150 mM KoAC, 5 mM DTT, 0.05% Tween20, 4 nM polymerase-streptavidin complex, and 100 nM primer template. The mixture was incubated on ice for 15 minutes prior to immobilization. Immobilization of the complex in a ZMW array chip was carried out on ice for one hour followed by five washes with 50 mM ACES pH 7.25, 120 mM KoAC, 5 mM DTT. The final wash buffer was removed prior to addition of the reaction buffer, which was the same as the wash buffer. The same buffer, but including additional components: 500 nM A555-O-dA6P, 500 nM A660-O-dC6P, 500 nM A647-O-dG6P, 0.015 mg/ml protocatechuate-3,4-dioxygenase, 4 mM protocatechuate, and 6 mM 3-nitrobenzoate was added to the chip to prepare for the sequencing reaction.

Template-directed sequencing was initiated by the addition of the prior reaction mixture but with manganese and A568-O-dT6P, that yielded a final concentration of 500 nM and 0.5 mM Mn-acetate. The reaction was observed for six minutes using a multiplexed confocal fluorescence detection system, e.g., as described in U.S. patent application Ser. No. 11/901,273, filed Sep. 14, 2007, the full disclosure of which is incorporated herein by reference in its entirety for all purposes, which detects fluorescent pulses upon incorporation of labeled nucleotides within the zero mode waveguides.

After the sequencing was complete, the data generated were subjected to various analyses to identify the sequences called, assess the quality of the reads, and assemble the various reads into a complete genomic sequence for phiX174. In total, 218,377 bases were aligned and the average depth of coverage was 40.5×. The average consensus accuracy was >99.9%. Three sequence variations that were originally deemed "errors" were subjected to additional analysis, including repeated sequencing and sequencing using conventional capillary sequencing systems (Sanger sequencing), and were found to represent actual variants in the phiX174 strain used as the template. There were no missing bases. In one aspect, these experiments showed that direct priming can be used with ZMW for genome sequencing applications. Subsequent analyses have sequenced the phiX174 genome to 100% accuracy and 60× coverage.

Example II

Sequencing of Lambda Genome

The lambda bacteriophage is a temperate bacteriophage that infects *Escherichia coli*. Its genome is 48,502 base pairs of double-stranded linear DNA. Sequencing of the lambda genome was performed using random primers rather than designed primers as described above for the phiX174 genome sequencing.

The lambda DNA was fragmented into 700-800 base pair fragments by random shearing. Specifically, the lambda DNA was diluted to 50 ng/µl in 50 mM MOPS, pH 7.5 and 150 mM potassium acetate. Two milliliters of the diluted lambda DNA was added to a nebulizer (Invitrogen), the pressure for input gas was set to 32 PSI (most of the data presented here), 20 PSI, or 10 PSI. The reaction was kept on ice while the nebulizer was running. The 32 PSI sample was nebulized for six minutes; and the 20 PSI and 10 PSI samples were nebulized for two minutes. A gel was run to determine the size of the fragments. (Variations on these experiments have also been performed, e.g., with sheared lambda DNA of 900-1500 base pairs; with sheared lambda DNA of 2500-4000 base pairs; and with a HindIII digest of lambda that produced fragments from 500 bp to 20 kb.)

After fragmentation, random nonomers were annealed in a solution of 50 ng/µl nebulized lambda DNA. A concentration of 3 µM random primers was found to work well. The mixture was heated to 95° C. for five minutes and subsequently snap-cooled by immediately placing the reaction in an ice bath. The annealed primer-lambda DNA complexes were kept on ice until loaded onto a ZMW chip. (Variations on this experiment have also been performed, e.g., with octomer random primers; and with octomer and nonomer primers containing three or four G's or C's on the 3' end.)

As with the phiX174 direct priming experiments, to first test whether the polymerase would extend the primed lamda DNA, extension reactions were performed by first diluting the primed template to 50 nM in reaction buffer (50 mM MOPS, pH 7.5; 150 mM potassium acetate; 5 mM DTT; 100 µM dATP, dCTP, dGTP; 25 µM ALEXA488-Chromatide dUTP (Invitrogen); 75 µM dTTP; and 1 mM MnCl2. Reactions were performed for 15 minutes at room temperature, and were quenched by addition of EDTA to final concentration of 50 mM. Extension products were analyzed by electrophoresis on a 0.7% agarose gel. Extension products were identified by incorporation of the ALEXA488-chromatide into large molecular weight DNA products as imaged on a Typhoon (GE/Amersham). These data demonstrated that the random primed lambda DNA does extend in bulk.

Polymerase was bound to the annealed primer-lambda DNA complexes in 50 mM MOPS pH 7.5, 150 mM KoAC, 5 mM DTT, and 4 nM polymerase-streptavidin complex, with 100 nM primer template. The mixture was incubated on ice for 15 minutes.

The primers annealed to the lambda DNA were pre-extended in the absence of a T analog with the bound polymerase enzyme by adding to final concentration of 500 nM Alexa555-O-dA6P, 500 nM A660-O-dC6P, 500 nM A647-O-dG6P and 1 mM Mn-Acetate. The primers were extended on ice for 5 minutes prior to immobilization to a ZMW chip by incubation on ice for 30 minutes followed by five washes with 50 mM ACES pH 7.25, 120 mM KoAC, 5 mM DTT. The sequencing reactions were carried out as with Example 1, except that observation was carried out for seven minutes.

After the sequencing was complete, the data generated were subjected to various analyses to identify the sequences called, assess the quality of the reads, and assemble the various reads into a complete genomic sequence for lambda. The ZMW sequencing of the random primed lambda template yielded 30.8× coverage (~1.493 Million bases). The average consensus accuracy was >98.8. There was one gap (186 total missing bases).

What is claimed is:

1. A method of sequencing nucleic acids, comprising;
   a) providing a sample comprising target nucleic acids;
   b) adding a set of primers to said sample, wherein the set comprises primers having different nucleotide compositions;
   c) contacting the target nucleic acids in the sample with the set of primers under conditions that promote hybridization to generate a set of target-primer complexes;
   d) using a polymerase enzyme, pre-extending primers in the target-primer complexes to generate pre-extended target-primer complexes that further comprise the polymerase enzyme;
   e) confining each of the pre-extended target-primer complexes to a separate reaction site on a substrate comprising a plurality of reaction sites;
   f) initiating template-directed synthesis of nascent nucleic acid strands from each of the pre-extended target-primer complexes, wherein the nascent nucleic acid strands are complementary to the target nucleic acids, and wherein the template-directed synthesis is performed by the polymerase enzyme;
   g) detecting processive incorporation of nucleotides into each of the nascent nucleic acid strands with no intervening buffer exchange during the template-directed synthesis, wherein the detecting further identifies nucleotide sequence reads for the nascent nucleic acid strands; and
   h) based upon the results of step f, determining a nucleotide sequence of the target nucleic acids.

2. The method of claim 1, wherein each of the plurality of reaction sites is positioned such that a signal emitted from any one reaction site is optically resolvable from any other signals emitted from any other of the plurality of reaction sites.

3. The method of claim 2, wherein the substrate comprises a plurality of optical confinements, each of which contains a single one of the plurality of reaction sites.

4. The method of claim 1, wherein the confining is performed through immobilization of each one of the target nucleic acids within the pre-extended target-primer complexes to the substrate.

5. The method of claim 4, wherein the immobilization comprises hybridization of each one of the target nucleic acids within the pre-extended target-primer complexes to a complementary oligonucleotide bound to the substrate.

6. The method of claim 4, wherein the immobilization comprises binding the polymerase enzyme within each of the pre-extended target-primer complexes to the substrate.

7. The method of claim 1, wherein the template-directed synthesis is catalyzed by an enzyme selected from the group consisting of a DNA polymerase, an RNA polymerase, and a reverse transcriptase.

8. The method of claim 7, wherein the enzyme is capable of strand displacement.

9. The method of claim 7, wherein the enzyme is thermostable.

10. The method of claim 7, wherein the enzyme has a processivity of at least 500 base pairs.

11. The method of claim 1, wherein the detecting comprises detecting signals from single target-primer complexes that further comprise the polymerase enzyme, wherein the signals are indicative of the identity of a nucleotide incorporated during the template-directed synthesis.

12. The method of claim 1, wherein the set of primers is a set of random primers.

13. The method of claim 1, wherein the set of primers is designed to anneal to selected regions of the target nucleic acids.

14. The method of claim 1, wherein the target nucleic acids are not subjected to amplification prior to said template-directed synthesis.

15. The method of claim 1, wherein the target nucleic acids are not subjected to cloning prior to said template-directed synthesis.

16. The method of claim 1, wherein the target nucleic acids are subjected to fragmentation prior to said template-directed synthesis.

17. The method of claim 1, wherein the nucleotide sequence of the target nucleic acids is not known prior to said template-directed synthesis.

18. The method of claim 1, wherein the target nucleic acids comprise genomic DNA.

19. The method of claim 1, wherein the target nucleic acids comprise RNA.

20. The method of claim 1, wherein the target nucleic acids are circular nucleic acids.

21. A method of generating sequence information for a target nucleic acid, comprising:
   a) providing a plurality of nucleic acid templates corresponding to the target nucleic acid;
   b) providing multiple primers that anneal to the nucleic acid templates;
   c) annealing the multiple primers to multiple locations on the nucleic acid templates;
   d) contacting the nucleic acid templates with single polymerase enzymes that bind at single primers annealed to the nucleic acid templates to generate primer-template-polymerase complexes;
   e) using the polymerase enzymes, pre-extending primers in the primer-template-polymerase complexes to generate pre-extended primer-template-polymerase complexes;
   f) confining each of the pre-extended primer-template-polymerase complexes to separate reaction sites on a substrate comprising a plurality of reaction sites;
   g) performing sequence-by-synthesis reactions to determine nucleotide sequences of the nucleic acid templates within the pre-extended primer-template-polymerase complexes, wherein the performing comprises identifying bases complementary to the nucleic acid templates by detecting labels that are released from said bases upon incorporation of said bases into nascent strands complementary to the nucleic acid templates; and
   h) assembling an overall nucleotide sequence of the target nucleic acid from the nucleotide sequences of the nucleic acid templates.

22. The method of claim 21, wherein the plurality of nucleic acid templates corresponding to the target nucleic acid comprises multiple overlapping fragments with nucleotide sequences identical to portions of the target nucleic acid.

23. The method of claim 21, wherein the nucleic acid templates are circular nucleic acid templates that are repeatedly processed in the sequence-by-synthesis reactions to generate multiple copies of the nucleotide sequences of the nucleic acid templates for use in step h.

24. The method of claim 21, wherein the nucleic acid templates are linear nucleic acids and the method further comprises repeating steps c, d, e, f, and g multiple times to determine multiple nucleotide sequences from each of the nucleic acid templates downstream of multiple single primers annealed to the nucleic acid templates for use in step h.

25. The method of claim 1, wherein the target nucleic acids are circular nucleic acid templates that are repeatedly processed in the sequence-by-synthesis reactions to generate multiple copies of the nucleotide sequences of the nucleic acid templates for use in step h.

26. The method of claim 21, wherein the confining comprises binding the polymerase enzymes within the pre-extended primer-template-polymerase complexes to the separate reaction sites on the substrate.

27. The method of claim 1, wherein the pre-extension is performed in the presence of at least three different dNTPs or analogs thereof.

28. The method of claim 21, wherein the pre-extension is performed in the presence of at least three different dNTPs or analogs thereof.

* * * * *